United States Patent
Belcher et al.

(10) Patent No.: US 10,151,716 B2
(45) Date of Patent: Dec. 11, 2018

(54) SYSTEM AND METHOD FOR INTERNAL INSPECTION OF RAIL COMPONENTS

(71) Applicant: GEORGETOWN RAIL EQUIPMENT COMPANY, Georgetown, TX (US)

(72) Inventors: Jeb E. Belcher, Georgetown, TX (US); Gregory Thomas Grissom, Georgetown, TX (US); James Edward Baciak, Gainesville, FL (US); Kelly Alexander Jordan, Gainesville, FL (US); Jyothier Nimmagadda, Gainesville, FL (US); Shuang Cui, Gainesville, FL (US); Michele Viola Manuel, Gainesville, FL (US)

(73) Assignee: GEORGETOWN RAIL EQUIPMENT COMPANY, Georgetown, TX (US)

( * ) Notice: Subject to any disclaimer, the term of this patent is extended or adjusted under 35 U.S.C. 154(b) by 134 days.

(21) Appl. No.: 15/228,481

(22) Filed: Aug. 4, 2016

(65) Prior Publication Data

US 2017/0038316 A1  Feb. 9, 2017

Related U.S. Application Data

(60) Provisional application No. 62/201,888, filed on Aug. 6, 2015.

(51) Int. Cl.
*G01N 23/204* (2006.01)
*B61K 9/10* (2006.01)
(Continued)

(52) U.S. Cl.
CPC .......... *G01N 23/204* (2013.01); *B61K 9/10* (2013.01); *G01N 23/203* (2013.01); *G01N 33/20* (2013.01); *G01T 3/00* (2013.01); *G01N 9/24* (2013.01)

(58) Field of Classification Search
CPC ...... B61K 9/10; G01N 23/203; G01N 23/204; G01N 33/20; G01N 9/24; G01T 3/00
See application file for complete search history.

(56) References Cited

U.S. PATENT DOCUMENTS 4,198,164 A * 4/1980 Cantor .................. B61K 9/08
250/202
4,794,256 A * 12/1988 DiMartino ............ G01F 23/288
250/357.1

(Continued)

FOREIGN PATENT DOCUMENTS

JP  H0627249  2/1994

OTHER PUBLICATIONS

European Patent Office; International Searching Authority; International Search Report and Written Opinion for Application No. PCT/US2016/045768 dated Jan. 4, 2017.

(Continued)

*Primary Examiner* — Marcus Taningco
(74) *Attorney, Agent, or Firm* — Parsons Behle & Latimer

(57) ABSTRACT

An internal imaging system has a radiation source and a plurality of detectors positioned to receive portions of the plurality of collimated beams that have been attenuated by interaction with the target. The radiation source is configured to irradiate a target with a plurality of collimated beams of radiation. Two of the plurality of collimated beams of radiation may have different beam shapes. Another internal imaging system includes a radiation source configured to irradiate a target with at least one collimated beam of
(Continued)

radiation and at least one detector. A planar rotating collimator is positioned adjacent to the radiation source and is configured to form the at least one collimated beam. The at least one detector is positioned to receive attenuated portions of the at least one collimated beam. The radiation source may be or include a neutron source. The detectors may be or include a plurality of neutron converters.

30 Claims, 19 Drawing Sheets

(51) Int. Cl.
  G01N 23/203 (2006.01)
  G01N 33/20 (2006.01)
  G01T 3/00 (2006.01)
  G01N 9/24 (2006.01)

(56) References Cited

U.S. PATENT DOCUMENTS

| | | | |
|---|---|---|---|
| 5,493,596 A | 2/1996 | Annis | |
| 5,838,759 A * | 11/1998 | Armistead | B66C 19/007 378/57 |
| 6,192,104 B1 * | 2/2001 | Adams | G01N 23/203 378/149 |
| 6,453,007 B2 * | 9/2002 | Adams | G01N 23/203 378/146 |
| 2003/0201394 A1 * | 10/2003 | Peoples | B66C 19/002 250/336.1 |
| 2006/0043310 A1 * | 3/2006 | Arsenault | G01N 23/20008 250/393 |
| 2008/0014643 A1 | 1/2008 | Bjorkholm | |
| 2010/0111255 A1 | 5/2010 | Harding | |
| 2013/0191070 A1 * | 7/2013 | Kainer | B61K 9/08 702/167 |
| 2013/0202090 A1 | 8/2013 | Belcher | |
| 2013/0230139 A1 * | 9/2013 | Morton | G01V 5/0066 378/57 |
| 2015/0198544 A1 * | 7/2015 | Alzaidi | G01N 23/204 250/370.12 |

OTHER PUBLICATIONS

European Patent Office International Searching Authority; Partial International Search Report issued in PCT Application No. PCT/US2016/045768 dated Oct. 20, 2016.

* cited by examiner 0.2 CM COLLIMATION 1e5 EVENTS PER 0.25 DEG ANGLE RES, 0.25 CM SCAN RES 0.2 CM COLLIMATION 1e5 EVENTS PER 0.25 DEG ANGLE RES, 0.25 CM SCAN RES 0.2 CM COLLIMATION 1e5 EVENTS PER 0.25 DEG ANGLE RES, 0.25 CM SCAN RES

SYSTEM AND METHOD FOR INTERNAL INSPECTION OF RAIL COMPONENTS

RELATED APPLICATION DATA

The present application claims the benefit of priority under 35 U.S.C. § 119 to U.S. Provisional Application No. 62/201,888, filed Aug. 6, 2015, entitled "System and Method for Internal Inspection of Rail Components Using x-ray and Neutron Imaging Techniques," the disclosure of which is incorporated herein by reference in its entirety.

BACKGROUND

Field of Disclosure

The embodiments described herein relate generally to the internal inspection of railway track components using x-ray and neutron imaging techniques. More particularly, the embodiments described herein relate to backscatter and transmission radiography techniques for internal inspection of railway track components.

Related Art

Currently, flaws in rails and other railway track components are detected through direct contact non-destructive methods, such as ultrasound, or through destructive methods. The negative consequences of the latter are obvious whereas the former may leave flaws undetected in the rail, or identify "false positives" when in fact no defect exists. One known way to detect these flaws is with a handheld ultrasound system.

Currently, some flaws may be detected using destructive methods. One such flaw is an under shell fracture in a rail that may not be detectable with known non-destructive method. Such a defect is important to find so as to prevent catastrophic rail failure leading to derailment of rail bound vehicles. Additional flaws may include Rail Base Corrosion (RBC). Although RBC can be found on any track, it is most prevalent in tunnels and/or where the track is electrified. This is due to the combination of the standing water and electricity flowing through the rail acting to rust and erode the rail-base at an increased rate.

Approximately 15.3% of all derailments between 2001 and 2010 were caused by broken rails or welds. The second most common cause of derailments accounted for only 7.3%, leaving the detection of rail flaws as the most significant factor for the reduction of train derailments. Known inspection methods may leave flaws undetected, leaving significant room for improvement.

SUMMARY

The present disclosure is directed to an internal imaging system and method that overcomes some of the problems and disadvantages discussed above.

An internal imaging system having a radiation source and a plurality of detectors. The radiation source is configured to irradiate a target with a plurality of collimated beams of radiation. At least two of the plurality of collimated beams of radiation may have different beam shapes. The plurality of detectors are positioned to receive portions of the plurality of collimated beams that have been attenuated by interaction with the target.

The plurality of detectors may include at least one transmission detector positioned to receive a target between the at least one transmission detector and the radiation source. The plurality of detectors may include at least one scatter detector positioned to receive radiation scattered by interaction with the target. The radiation source and the plurality of detectors may be mounted upon a vehicle. The vehicle may be a rail traversing vehicle. The radiation source may be or include a neutron source and the plurality of detectors may be or include a plurality of neutron converters. The plurality of collimated beams may include a rotating pencil beam and at least one fan beam. The at least one fan beam may be a plurality of fan beams. The rotating pencil beam may be positioned between two of the plurality of fan beams.

The system may include a collimating collar. The collimating collar may include at least one fan beam collimator, each of the at least one fan beam collimator having a channel shaped to form radiation passing though the channel into one of the at least one fan beam. The collimating collar may include a collimator wheel rotatably disposed around the radiation source. The collimator wheel may include a plurality of beam openings, wherein radiation passing through the plurality of beam openings as the collimator wheel rotates forms a rotating pencil beam.

The system may include a planar rotating collimator positioned adjacent to the radiation source and configured to form the plurality of collimated beams. The radiation source may include a fixed aperture having an opening shaped to form a first fan beam. The planar rotating collimator may include a pencil beam opening, wherein the first fan beam intersects a portion of the pencil beam opening.

A method of using an internal imaging system to inspect a target includes irradiating a target with a plurality of collimated beams of radiation. The plurality of collimated beams include a first beam having a first beam shape and a second beam having a second beam shape. The method includes detecting a strength of a portion of the first beam that has been attenuated by interaction with the target with at least one first detector, detecting a strength of a portion of the second beam that has been attenuated by interaction with the target with at least one second detector, and generating data relating to an internal characteristic of the target using the detected strengths.

The at least one first detector may include at least one transmission detector. The at least one first detector may include at least one scatter detector. The at least one second detector may include at least one transmission detector. The at least one second detector may include at least one scatter detector. The radiation source may be a neutron source and the at least one first detector and the at least one second detector may be neutron converters.

At least two of the plurality of collimated beams of radiation may have different beam shapes. The plurality of collimated beams may include a rotating pencil beam and at least one fan beam. The first beam may be a rotating pencil beam. The second beam may be a fan beam. The method may include determining an angular position of the rotating pencil beam. The method may include irradiating each of a plurality of targets with a plurality of collimated beams of radiation.

The method may include emitting radiation from a radiation source and receiving a portion of the emitted radiation into a channel of at least one fan beam collimator and forming at least one fan beam. The method may include rotating a collimator wheel having a plurality of beam openings and receiving another portion of the emitted radiation into the plurality of beam openings of the collimator wheel and forming a rotating pencil beam.

The method may include emitting radiation from a radiation source and collimating the emitted radiation to include a first fan beam. The method may include rotating a planar rotating collimator, the planar rotating collimator including a pencil beam opening shaped to intersect a portion of the first fan beam and form a rotating pencil beam. The method may include emitting radiation from a radiation source and collimating the emitted radiation to include at least one second fan beam. The planar rotating collimator may include at least one fan beam opening shaped to receive the at least one second fan beam when the at least one fan beam opening is aligned with the at least one second fan beam. The method may include producing a three-dimensional representation of the target from the data. The producing a three-dimensional representation of the target from the data may be at an off-site location.

Another internal imaging system includes a radiation source and at least one detector. The radiation source is configured to irradiate a target with at least one collimated beam of radiation. The radiation source is not an x-ray source. The radiation source may be a gamma source, neutron source, or other energy wave source. The at least one detector is positioned to receive attenuated portions of the at least one collimated beam.

The system may include a vehicle. The radiation source and the at least one detector may be connected or mounted to the vehicle. The vehicle may be configured to travel along a railway track. The radiation source may be a neutron source. The at least one detector may be at least one neutron converter. The at least one neutron converter may include a neutron scintillator. The at least one collimated beam may be a plurality of collimated beams. The plurality of collimated beams may include at least one fan beam and a rotating pencil beam. The at least one detector may include a transmission detector. The at least one detector may include a scatter detector.

An internal imaging system includes a radiation source, a planar rotating collimator, and at least one detector. The radiation source is configured to irradiate a target with at least one collimated beam of radiation. The planar rotating collimator is positioned adjacent to the radiation source and configured to form the at least one collimated beam. The at least one detector is positioned to receive attenuated portions of the at least one collimated beam.

The at least one collimated beam may be a plurality of collimated beams. The plurality of collimated beams may include at least one fan beam and a rotating pencil beam. The radiation source may include a fixed aperture having an opening shaped to form a first fan beam. The planar rotating collimator may include a pencil beam opening, wherein the first fan beam intersects a portion of the pencil beam opening. The fixed aperture may include an opening shaped to form at least one second fan beam. The planar rotating collimator may include at least one fan beam opening shaped to receive the at least one second fan beam when the at least one fan beam opening is aligned with the at least one second fan beam.

The system may include a vehicle. The radiation source and the at least one detector may be connected or mounted to the vehicle. The vehicle may be configured to travel along a railway track. The radiation source may be a neutron source. The at least one detector may be at least one neutron converter. The at least one neutron converter may include a neutron scintillator.

Figure 1:
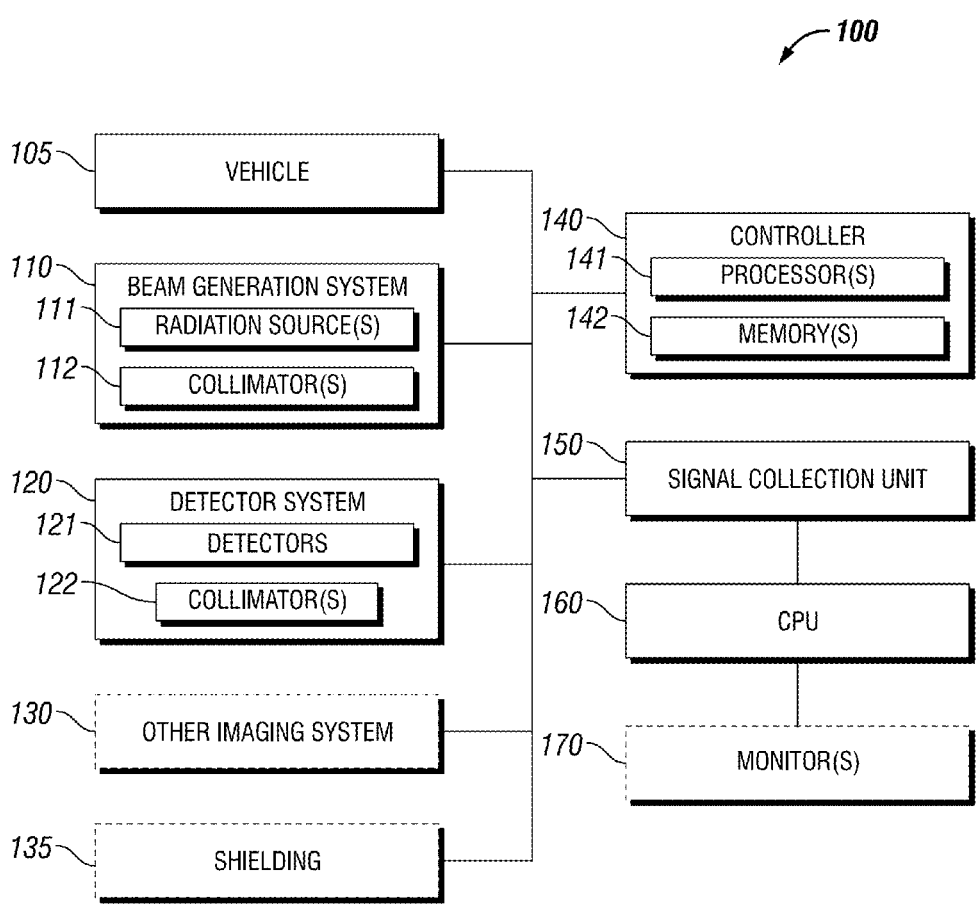
FIG. 1 shows a schematic view of an embodiment of an internal imaging system.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the scope of the disclosure as defined by the appended claims.

DETAILED DESCRIPTION

The embodiments described herein are directed to an internal inspection system for railway track components using x-ray and/or neutron radiographic technology. The internal inspection system, or at least a portion thereof, may be mounted to a rail traversing vehicle, such as a hi-rail, a rail car, a rail bound drone or an engine. The internal inspection system may be used alone or synchronized with a video scan or 4D camera scan to provide a surface scan which can correspond to the internal image. One such surface scanning system is the Aurora system from Georgetown Rail Equipment Company of Georgetown, Tex., and systems disclosed in U.S. patent application Ser. No. 14/599,757, filed on Jan. 19, 2015, and entitled "System and Method for Inspecting Railroad Ties" and published as U.S. Pat. No. 8,958,079, the disclosure of which is incorporated by reference in its entirety. The radiographic inspection and video or 4D camera scan may be synchronized by the use of a wheel encoder and/or GPS system. The GPS system may be used to locate a railway component. For example, GPS coordinates may be recorded during the inspection to facilitate later locating a damaged component for repair or replacement. The video scan may provide color images or grayscale images. Alternatively, a comparison, such as a side-by-side comparison, of the radiographic scan and a surface scan may be used to analyze railway components instead of super-imposing the surface scan onto the backscatter x-ray scan.

The present disclosure is directed to detecting problems and flaws in railway track components through non-destructive means. Other than rail inspection, it is anticipated that the system and method disclosed herein would be beneficial to detect flaws in, among other things, joint bars, switches, plates, fasteners, spikes, bridges, and tunnels. This system may be used in both installed rail environments such as active railroads, and mill environments where products are created.

The embodiments disclosed may be used to inspect, for example, material density; the length of cracks, voids, or other internal flaws; the width of cracks, voids, or other internal flaws; the height of cracks, voids, or other internal flaws; the volume of cracks, voids, or other internal flaws; and/or composition of composite materials. Additionally, the radiographic techniques may be used to determine other aspects of railway components. For example, radiographic techniques may be used to determine if spikes are cut below the plate, determine if reinforcing structures show signs of fatigue or decomposition, show material decomposition, and/or calculate structural support of an object. Collected data may be used to identify and/or analyze additional railway component features as would be recognized by one of ordinary skill in the art having the benefit of this disclosure. Additionally, neutron imaging technology may be used to determine other aspects of railway components that may not be able to be detected using x-ray technology. For example, neutron imaging technology may be used to determine the rust formation on a surface of a railway track component.

The internal inspection system may incorporate x-ray and neutron radiographic imaging techniques, or a combination thereof, to detect flaws in railway components more thoroughly and at an acceptable rate of speed than known systems and methods. The radiographic imaging techniques may be applied in multiple orientations and the results may be used to reconstruct or represent three-dimensional images of the same railway track components. The radiographic imaging techniques may include transmission radiography and scatter radiography. Scatter detectors, transmission detectors, or combinations thereof may be positioned around a target to be inspected. The detection of scattered radiation and transmitted radiation may be used together, as will be appreciated by one of ordinary skill in the art having the benefit of this disclosure.

Transmission radiography uses a radiation source, such as an x-ray source or neutron source, in conjunction with a transmission detector placed on an opposing side of the intended target. Transmission detectors are configured to receive radiation that has passed through the target. Radiation is emitted from the radiation source, passes through the target, and is received on the opposite side of the target by the transmission detector. The strength of the signal passing through the target is interpreted and used to analyze the target. Transmitted radiation may be used to determine the composition and density of materials, as well as the presence of cracks, voids, or other internal flaws.

Backscatter radiography uses scattered rays that bounce back from within the target. Backscatter radiography may use lower levels of energy than transmission radiography. In backscatter x-ray methods, a scatter detector receives some of the rays that bounce off the object. The scatter detectors are configured to receive scattered radiation corresponding to a particular element of the target. The strength of the signal reaching the detector is then interpreted and used to analyze the target. Scattered radiation may be used to determine the composition and density of materials. In addition, scattered radiation may be used to determine the presence of cracks, voids, or other internal flaws.

Neutron radiography may provide advantages over x-ray radiography. For example, neutron radiography may be used as a complementary non-destructive technique to x-ray radiography. However, unlike x-rays, neutrons interact with the nuclei of the atoms as they pass through. Neutrons may penetrate through heavy nuclides more easily when compared to x-rays. Neutrons may image the light nuclides and pass through heavy nuclides better than x-rays. Neutrons may also interact differently with different isotopes. As a result, x-ray radiography and neutron radiography may be capable of providing different information.

Neutron radiography uses a neutron source in conjunction with a neutron converter placed around the intended scanning target. The neutrons are emitted from the source, pass through and scatter off the target object. Highly collimated beam of neutrons attenuate when incident on the railway track components and are received by a converter. The strength of the signal reaching the converter is then interpreted and used to analyze the target. With respect to backscatter neutron radiography, the neutron converter may be positioned on the same side of the target object. The neutrons are emitted from the source and are scattered upon contact with the target. While a portion of the neutrons pass through the target with only minor deflection or without any deflection, some of the neutrons are deflected by the object back toward the neutron source. These deflected neutrons are received at the converter. The strength of the backscatter signal may be interpreted to analyze internal structure of the target. The backscatter neutron radiography may incorporate neutron diffractions and small angle scatterings to image the strain patterns in railway track components.

The neutron converter may be a neutron scintillator, such as a $^6$LiF—ZnS, or a neutron detector, such as a neutron sensitive micro channel plate (MCP) glass doped with $^{10}$B or Gadolinium offered for sale by NOVA Scientific of Sturbridge, Mass., or any other technology that converts neutrons to signals or pulses. The internal inspection system may include a charge coupled device (CCD) sensor and light reflection mirrors with an array of scintillation materials to produce either color or grayscale images. The neutron scintillator may be hydrogen rich organic scintillator, $^6$Li enriched scintillator, and other scintillator technology that converts neutrons to light signals. The resolution of the scintillators may be about 50 μm. Other neutron scintillation materials may be used.

The signals or pulses of a neutron converter may be used to produce either color or grayscale images of an internal structure of a target. The internal inspection system may include an array of individual neutron converters that are collimated like MCP and used with neutron detectors. MCPs may have a resolution of about 10 μm. The distances between the neutron source, the target, and the neutron converters may be varied to increase or decrease the resolution. The internal inspection system may be configured to scan railway components at preselected track speeds. The system may be configured to permit an increase or decrease in speed during the scan. For example, the speed may be decreased to improve resolution of a particular component, if desired.

The neutron source may be any source capable of emitting neutrons, such as a neutron generator, an accelerator, or a radioisotope that emits neutrons. The neutron generator for the internal inspection system may be an about 2.5 MeV deuterium-deuterium (DD) neutron system with approximately 125 kV of acceleration voltage and approximately 8 mA of beam current. The neutron yield of the DD neutron generator may be about $10^9$ neutrons per second. Also, a deuterium tritium (DT) neutron generator may be used for higher energy neutrons of about 14.1 MeV. In one embodiment, the inspection system may use a 125 kV, 8 mA neutron generator. The total system power consumption may be less than 2000 watts. The total power of the inspection system may be adjusted dynamically to increase or decrease exposure, as selected for penetration into the target and/or safety requirements. The x-ray energy for an x-ray source may reach 3 MeV. In order to provide power for the radiographic system, a scanning vehicle may be equipped with a separate generator. More than one scanning unit may be used and additional power sources may be included.

The speed of the scanning system may depend on multiple factors including the quantity of scanning units, FOV (field of view), resolution, and the amount of signal returning to the detectors. An operator may select a smaller FOV with a coarse resolution for a faster scanning speed. The scanning speed may be varied by changing the resolution at the time of operation through a signal collecting unit (SCU) that is dynamically adjustable. The SCU is configured to collect and transfer the images or signals produced by the neutron converters. In some embodiments, the system may be used for a multiple pass system. The first pass may be a course scan and after identifying areas of potential concern, a second pass with a finer scan may be made. The SCU may be an array of CCD cameras or fiber optic cables.

FIG. 1 shows a schematic view of an embodiment of the internal imaging system 100 having a beam generation system 110, a detector system 120, a signal collection unit ("SCU") 150, and a CPU 160. The beam generation system 110 includes the radiation source 111 and a collimator 112 configured to collimate radiation from the radiation source 111 and irradiate a target with at least one beam of penetrating radiation. The at least one beam of radiation may be a fan beam, cone beam, pencil beam, other beam shape, or combination thereof. The at least one beam may be a plurality of beams. At least two of the plurality of beams may have different beam shapes. The radiation source 111 may be an x-ray source, gamma source, neutron source, or other energy wave source, as would be appreciated by one of ordinary skill in the art having the benefit of this disclosure. The radiation source 111 may be configured to irradiate multiple targets. The multiple targets may be multiple railway components, such as both rails of a railroad track. The detector system 120 includes at least one detector 121 positioned to receive radiation transmitted through or scattered by the target. The at least one detector 121 is configured to measure radiation from the radiation source 111 that has been attenuated by interaction with the target. The radiation source 111 of the beam generating system 110 and the at least one detector 121 of detector system 120 may be configured to receive a portion of a railway component, such as a rail, there between such that at least a portion of the at least one beam of radiation pass through the railway component and are received by the at least one detector 121. The at least one detector 121 may be directed toward the railway component such that at least a portion of the radiation emitted from the radiation source 111 that is scattered by interaction with the railway component is received by the at least one detector 121. The at least one detector 121 may be positioned to receive scattered radiation in numerous directions. The strength of the signal received by the at least one detector 121 may be interpreted to analyze the internal structure of the target. The system 100 may further include any of the systems or structures described herein, for example, one or more other imaging or scanning systems 130. The other imaging system 130 may provide a surface scan, as described above.

At least a portion of the system 100 may be mounted to or receivable by the vehicle 105. The vehicle 105 may be confined to travel along a predefined path. The vehicle 105 may be a rail traversing vehicle, such as a hi-rail truck, adapted to travel along the rails of a railway. The inspection system 100 may be mounted or otherwise connected to the vehicle 105 in various ways, such as to the front of the vehicle 105 or the back of the vehicle 105. The inspection system 100 may be mounted in or upon the vehicle 105 and directed beneath the vehicle 105. The radiation source 111 of the beam generating system 110 may be positioned with sufficient clearance to avoid obstacles located on the path of travel. The distances between the radiation source 111, the target, and the detectors 121 may be varied to increase or decrease the resolution. The position of the radiation source 111 and a detector 121 may be adjusted to limit inspection to an area of interest, such as a specific railway component or a portion of the railway component. The inspection system 100 may include collimators 122 configured to limit the field of view of a detector 121. The inspection system 100 may include shielding 135 configured to absorb scattered radiation that may otherwise escape the system in an unintended direction.

The beam generation system 110 and the detector system 120 may include a transmission x-ray scanning system, a backscatter x-ray scanning system, a transmission neutron radiography scanning system, a backscatter neutron radiography scanning system, or a combination thereof. In a transmission x-ray scanning system, the radiation source 111 includes an x-ray source and the at least one detector 121 includes an x-ray transmission detector positioned to receive an attenuated portion of an x-ray beam after it has passed through the railway component. In a backscatter x-ray scanning system, the radiation source 111 includes an x-ray source and the at least one detector 121 includes at least one x-ray backscatter detector positioned to receive radiation that has been scattered by interaction with the railway component. In some embodiments, the internal imaging system 100 includes both a transmission x-ray scanning system and a backscatter x-ray scanning system. In some embodiments, the transmission x-ray scanning system and the backscatter x-ray scanning system may share at least one x-ray source or at least one detector.

In a transmission neutron radiography scanning system, the radiation source 111 includes a neutron source and the at least one detector 121 includes a neutron transmission converter positioned to receive an attenuated portion of a neutron beam after it has passed through the railway component. In a backscatter neutron radiography scanning system, the radiation source 111 includes a neutron source and the at least one detector 121 includes at least one neutron backscatter converter positioned to receive radiation that has been scattered by interaction with the railway component. In some embodiments, the internal imaging system 100 includes both a transmission neutron radiography scanning system and a backscatter neutron radiography scanning system. The transmission neutron radiography scanning system and the backscatter neutron radiography scanning system may share at least one neutron source or at least one neutron converter. In some embodiments, the internal imaging system 100 includes both x-ray and neutron sources. A single radiation source may provide multiple beams of radiation. The internal imaging system 100 may include additional radiation sources directed to other railway track components, such as the other rail, for inspection.

In some embodiments, the internal imaging system 100 further includes a controller 140 to initiate operations as described herein. The controller 140 may include one or more processors 141 and one or more memories 142. The one or more memories 142 may store instructions that, when executed by the one or more processors 141, cause the one or more processors 141 to initiate the operations. The operation may include controlling at least one of the beam generation system 110 and the detector system 120. The operations may include receiving information from at least one of the beam generation system 110 and the detector system 120. The operations may include initiating scanning of a selected railway component.

The internal imaging system 100 may include a signal collection unit (SCU) 150 configured to collect and transfer the images or signals produced by the detectors 121. The SCU 150 may also collect and transfer images produced by the other imaging system 130. The SCU 150 may be an array of CCD cameras or fiber optic cables. The detector signals may be synchronized with a location by the use of a wheel encoder and/or GPS system. The internal imaging system 100 may include at least one computer processing unit (CPU) 160 in communication with the detectors 121 through the SCU 150. In some embodiments, the controller 140 may be integral to the CPU 160. Data is generated as each of the detectors 121 detects the transmitted or scattered radiation. This data may be a pixelated internal image or a signal from the detector 121. The CPU 160 receives the data from the detectors 121 through the SCU 150 and the CPU 160 may analyze the data to determine potential flaws and/or defects within the target.

In some embodiments, the analyzing and processing may be performed on the same CPU 160 or a separate CPU in a different location from the detectors 121. For example, the radiation source 111 of the beam generation system 110 and the detectors 121 of the detector system 120 may be mounted to a rail traversing vehicle 105 and collect data from the detectors 121. The data from the detectors 121 may be stored and later processed off-site. In some embodiments, the data may be processed on-site. The CPU 160 may be programmed with various algorithms used to analyze the detection data and identify potential flaws and/or defects in the internal structure of the target. The CPU 160 may be in wired or wireless communication with the detectors 121. Multiple CPUs 160 may be used to store and/or analyze data generated by the detectors 121. A display or monitor 170 may be connected to the CPU 160 and an image may be displayed on the monitor 170 based on the data received by the CPU 160. The monitor 170 may display the pixelated internal image or a reconstructed image of the target(s) for analysis and review by an operator and, in some embodiments, superimpose the internal image of the railway component on another image of the railway component. In some embodiments, the monitor 170 may be positioned within a cab of the vehicle 105 and be viewed by the operator during inspection.

Figure 2:
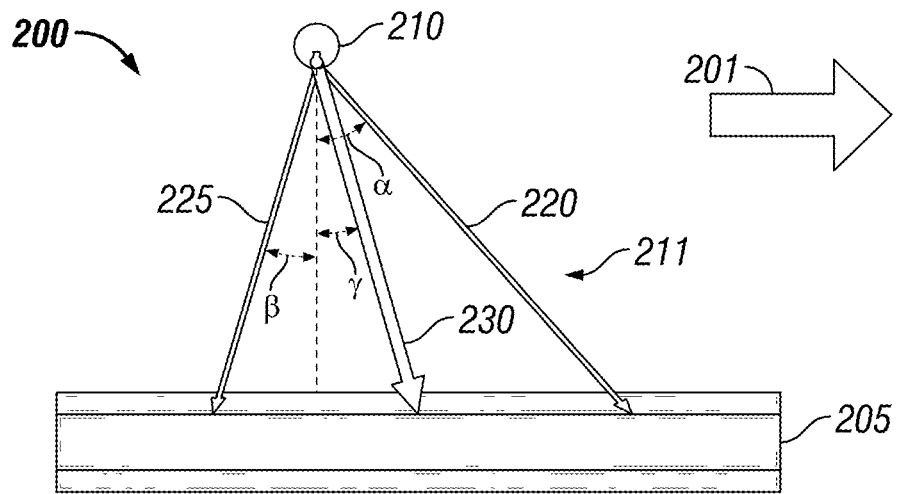
FIG. 2 shows a top view of an embodiment of a beam generation system.

FIG. 2 shows a top view of an embodiment of a beam generation system 200 that includes at least one radiation source 210. The radiation source 210 may be a neutron source. The radiation source 210 may be an x-ray source, gamma source, or other energy wave source, as would be appreciated by one of ordinary skill in the art having the benefit of this disclosure. The direction of travel of beam generation system 200 is indicated by arrow 201. The radiation source 210 may include a collimator (not shown in FIG. 2) and produce at least one beam 211 of radiation. The at least one beam 211 may be a plurality of beams 211 of radiation. The radiation source 210 is positioned to direct the beams 211 of radiation into a railway component. Each beam 211 may be positioned perpendicular to or at an angle with respect to the railway component to be inspected. The railway component may be various railway components, such as a rail 205. The beams 211 of radiation may be directed into a specific portion of the railway component, such as the head, base, or web of the rail 205. The radiation source 210 may irradiate multiple targets, or multiple portions of the same target, at the same time, and may be moved along a path of travel to inspect and analyze the internal structure thereof.

Figure 3:
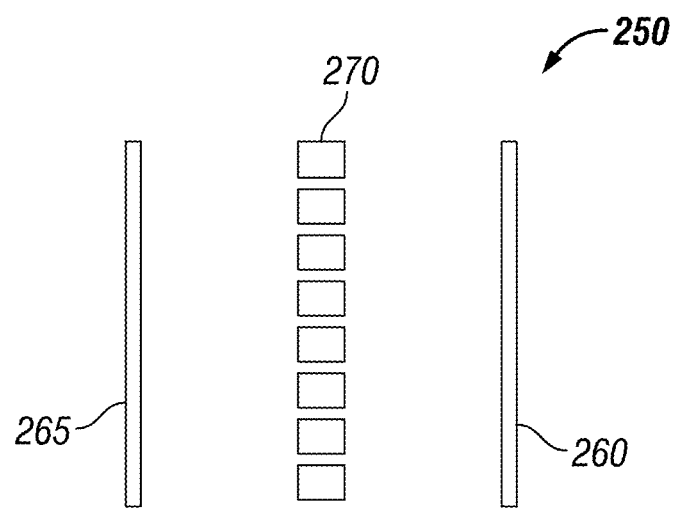
FIG. 3 shows an embodiment of a radiation profile of a beam generation system directed toward a rail of a railroad track.

The beams 211 of radiation may be fan beams, cone beams, pencil beams, other beam shapes, or combination thereof. The plurality of beams 211 may include at least two beams having a different beam shape. The plurality of beams 211 may include at least one fan beam and at least one pencil beam. The at least one fan beam may be a plurality of fan beams. As shown, beams 211 of beam generation system 200 may include one pencil beam 230, a forward fan beam 220, and a rearward fan beam 225. Some embodiments may include more than two fan beams. The pencil beam 230 may be positioned between the forward fan beam 220 and the rearward fan beam 225. The forward fan beam 220 may be directed at an angle α with respect to the normal of the rail 205. The angle α may range from 0 to 45 degrees. The rearward fan beam 225 may be directed at an opposing angle β with respect to the normal of the rail 205. The angle β may range from 0 to 45 degrees. In some embodiments, both the forward fan beam 220 and the rearward fan beam 225 are oriented in the same direction, but at different angles. The rotating pencil beam 230 may be directed at an angle γ with respect to the normal of the rail 205. The angle γ may range from −45 degrees to +45 degrees. The total scan span angle between forward fan beam 220 and rearward fan beam 225 may be less than or equal to 90 degrees. The orientation and the intensity of the pencil beam 230 and the fan beams 220, 225 may be adjusted to increase the resolution of the reconstruction. In some embodiments, the angle α of the forward fan beam 220 may be 45 degrees and the angle θ of the rearward fan beam 225 may be 30 degrees. As described below, data from multiple perspectives is recorded and used to reconstruct flaws within the target. As shown in FIG. 3, the beam generation system 200 generates a radiation profile 250. The radiation profile 250 includes a forward fan beam profile 260 corresponding to the forward fan beam 220, a rearward fan beam profile 265 corresponding to the rearward fan beam 225, and a pencil beam profile 270 corresponding to the pencil beam 230. As discussed below, the combination of a fan beam profile and a pencil beam profile may be advantageous to generate a localized set of information, as well as a broader set of information, to be used during reconstruction.

Figure 4:
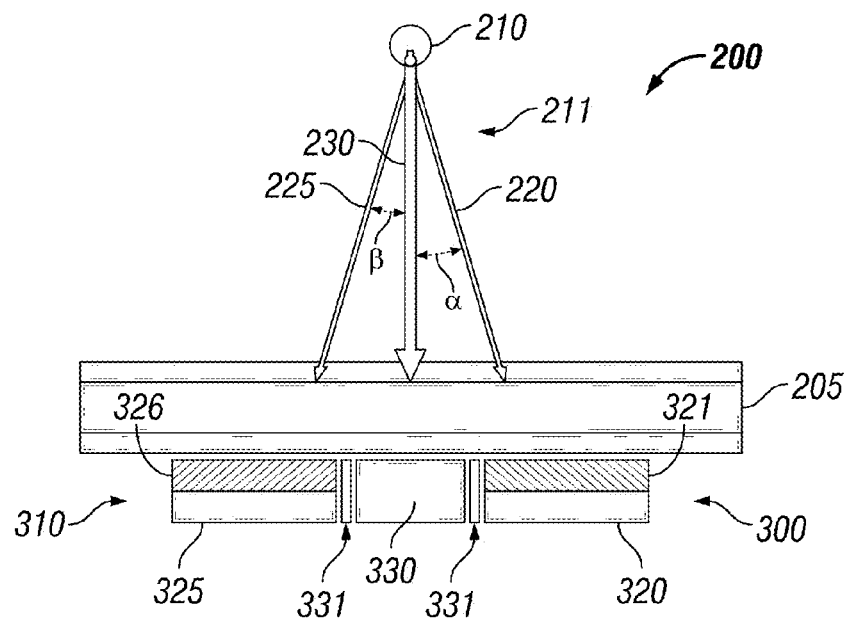
FIG. 4 shows an embodiment of a beam generation system and a detector system configured to detect radiation that has been transmitted through a railway component.

FIG. 4 shows an embodiment of the beam generation system 200 and a detector system 300 configured to detect radiation that has been transmitted through a railway component, such as a rail 205. As shown in FIG. 4, the angle α of the forward fan beam 220, the angle β of the rearward fan beam 225, and the angle γ (shown as zero degrees) of the pencil beam 230 of the beam generation system 200 are different from FIG. 2 for illustrative purposes. However, it is appreciated that the detector system 200 may also be used with the beam angles displayed in FIG. 2 and described above. In operation, the beams 211 of radiation from beam generation system 200 are directed into rail 205. The beams 211 include a forward fan beam 220, the rearward fan beam 225, and the pencil beam 230. As the beams 211 of radiation are transmitted through the rail 205, the beams 211 are attenuated. The detector system 300 may include transmission detectors 310, scatter detectors 311 (shown in FIGS. 5 and 6), or combinations thereof. The transmission detectors 310, such as x-ray transmission detectors and neutron transmission converters, are configured to measure an attenuated portion of the beams 211 of radiation. The transmission detectors 310 may be a bank of detectors positioned along the rail 205 to receive different portions of the beams 211 of radiation. The transmission detectors 310 may include a forward beam detector 320, a pencil beam detector 330, and a rearward beam detector 325. As shown in FIG. 4, the pencil beam detector 330 is positioned to receive the attenuated portion of the pencil beam 230, forward beam detector 320 is positioned to receive the attenuated portion of the forward fan beam 220, and the rearward beam detector 325 is positioned to receive the attenuated portion of the rearward fan beam 225. The strength of the signals from the transmission detectors 310 is interpreted and used to analyze characteristics of the target.

Each transmission detector 310 may include collimators configured to limit the field of view of the transmission detector 310. For example, collimators 326 may be positioned between the rearward fan beam 225 and rearward beam detector 325. As radiation of the rearward fan beam 225 passes through the rail 205 at angle α, the attenuated portion is received into the collimators 326 and passes to the rearward beam detector 325. Scattered radiation from other beams may be absorbed or blocked by the collimators 326 from reaching the rearward beam detector 325. The collimators 321 may be positioned between the forward fan beam 220 and the forward beam detector 320. As radiation of the forward beam 220 passes through the rail 205 at angle β, the attenuated portion is received into the collimators 321 and passes to the forward beam detector 320. Scattered radiation from other beams may be absorbed or blocked by the collimators 321 from reaching the forward beam detector 320. The pencil beam detector 330, which is positioned to receive the attenuated portion of the pencil beam 230, may not include collimators. For example, if the pencil beam 230 is directed perpendicular to the rail 205 and the fan beams 220, 221 are directed away from the pencil beam 230, a collimator may not be needed. However, in some embodiments, collimators may be associated with the pencil beam detector 330 as would be appreciated by one of ordinary skill in the art having the benefit of this disclosure. The pencil beam detector 330 may be separated from the forward beam detector 320 and the rearward beam detector 325 by dividers 331 that absorb or block the type of radiation from the radiation source 210.

Figure 5:
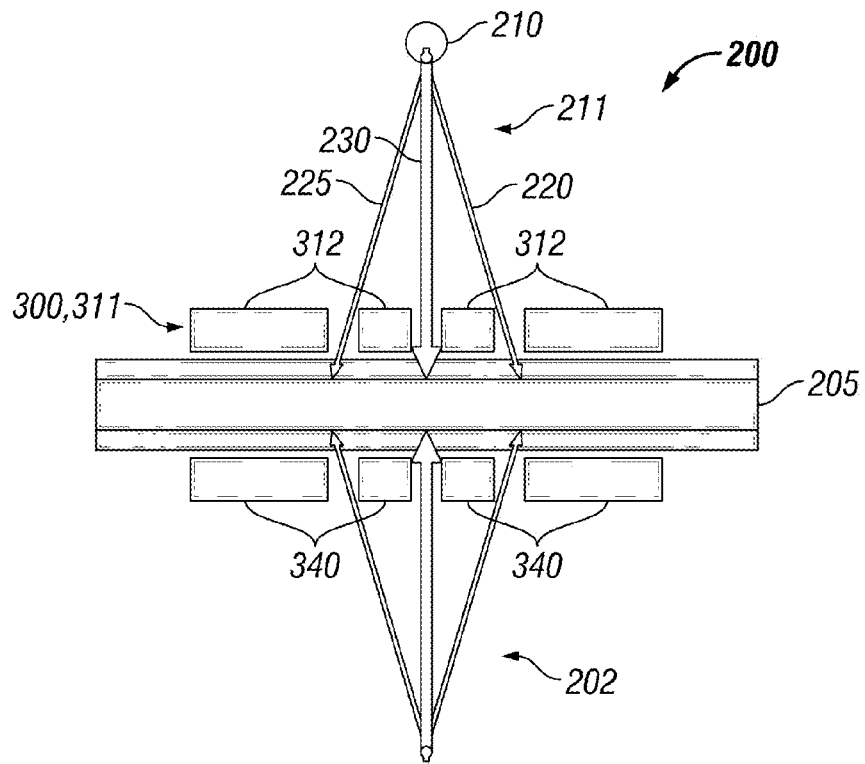
FIG. 5 shows an embodiment of a beam generation system and a detector system configured to detect radiation that has been scattered by interaction with the railway component.

FIG. 5 shows an embodiment of the beam generation system 200 and a detector system 300 configured to detect radiation that has been scattered by interaction with the railway component. In operation, the beams 211 of radiation from the beam generation system 200 are directed into the rail 205. The beams 211 include a forward fan beam 220, the rearward fan beam 225, and the pencil beam 230. As the beams 211 of radiation are transmitted through the rail 205, the radiation is scattered by elements of the rail 205. The detector system 300 may include scatter detectors 311, such as x-ray scatter detectors and neutron scatter converters, positioned to detect radiation that has been scattered. The scatter detectors 311 may be positioned along the rail 205 to receive different scattered portions of the beams 211 of radiation. The scatter detectors 311 may be positioned to receive scattered radiation in numerous directions. The scatter detectors 311 may include backscatter detectors 312 positioned adjacent to the beams 211 to receive backscattered radiation. Each scatter detector 311 may include collimators configured to limit the field of view of the scatter detector 311. The strength of the signals from the scatter detectors 311 is interpreted and used to analyze characteristics of the target.

As shown in FIG. 5, some embodiments may include a second beam generation system 202 and additional backscattered detectors 340 positioned on the opposing side of the rail 205 from the beam generation system 200. The additional backscatter detectors 340 are positioned to detect radiation that has been scattered from the second beam generation system 202. In some embodiments, the radiation inspection system 200 and the second beam generation system 202 may be offset and/or have a radiation source of a different type.

Figure 6:
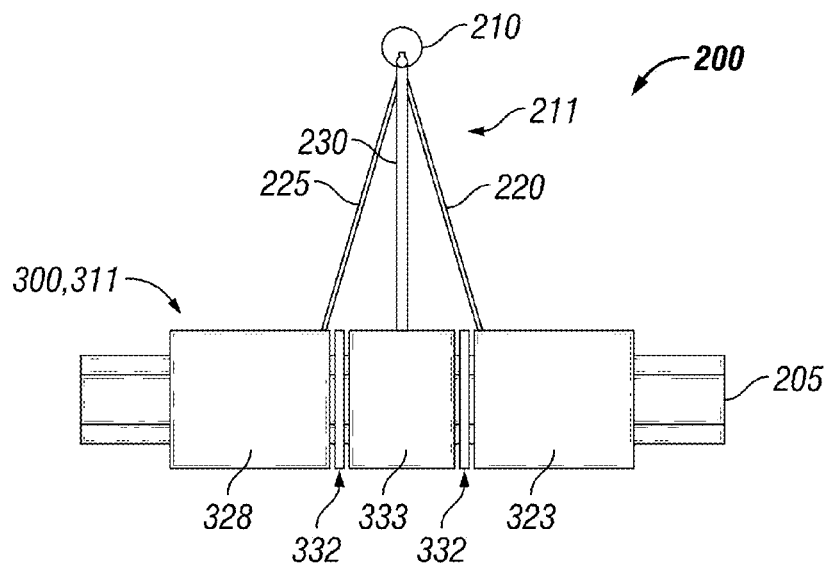
FIG. 6 shows an embodiment of a beam generation system and a detector system configured to detect radiation that has been scattered above a railway component.

FIG. 6 shows an embodiment of the beam generation system 200 and a detector system 300 configured to detect radiation that has been scattered above the rail 205. As shown, the scatter detectors 311 of detector system 300 may include a forward top scatter detector 323, a middle top scatter detector 333, and a rearward top scatter detector 328 positioned along the top of the rail 205 to receive different scattered portions of the beam 211 of radiation. The middle top scatter detector 333 may be separated from forward top scatter detector 323 and rearward top scatter detector 328 by dividers 332 that absorb or block the type of radiation from the radiation source 210. The strength of the signals from the scatter detectors 311 is interpreted and used to analyze characteristics of the target.

Figure 7:
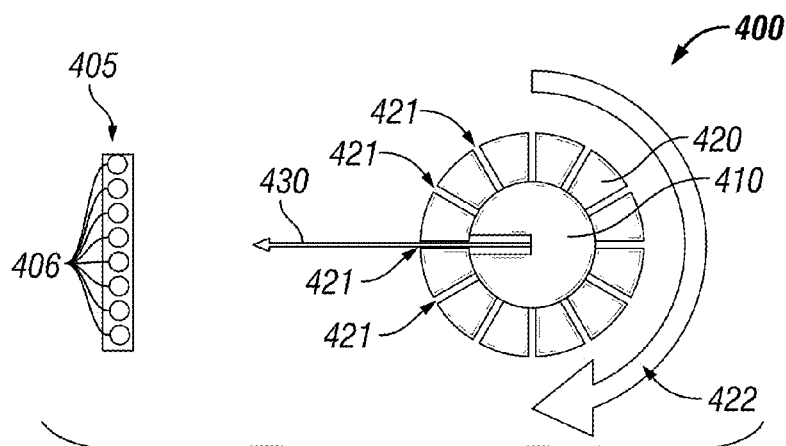
FIG. 7 shows an embodiment of a pencil beam system.

FIG. 7 shows an embodiment of a pencil beam system 400 configured to generate a pencil beam 430. The pencil beam system 400 includes a radiation source 410 and a rotating aperture 420. The pencil beam 430 is a narrow beam of radiation that may be used for illuminating discrete portions 406 of a target 405. By illuminating only the portions 406 of the target 405, the radiation dose may be reduced as well as produce a localized set of information for detectors or converters to receive. The amount of information captured using the pencil beam 430 is proportional to its speed relative to the target 405 being inspected. Higher speeds increase the distance between imaged portions 406 of the target 405.

Radiation may be emitted from the radiation source 410 through a fixed collimator (not shown in FIG. 7) and through the rotating aperture 420 to form the pencil beam 430. The fixed collimator and the rotating aperture 420 work in conjunction to direct radiation to the desired portions 406 of the target 405. The fixed collimator restricts the emission of unwanted radiation. The rotating aperture 420 focuses and directs the radiation. The rotating aperture 420 includes openings 421 that collimate radiation into pencil beam 430 and direct the pencil beam 430 toward the target 405. As the rotating aperture 420 turns in direction 422, the pencil beam 430 is swept through all of the angles to illuminate the target 405. This rotation can be a full revolution, or may be a back and forth motion. The rotational position of the pencil beam 430 is monitored by the system 400 and may use an electrical impulse, such as an encoder, to determine the angle of the pencil beam 430 as it is emitted from the radiation source 410. The beam angle and information received by a radiation detector may be used to reconstruct the image from the series of angular illuminations. In some embodiments, the rotating aperture 420 may be a collimation collar 520 (shown in FIG. 8) or a planar rotating collimator 620 (shown in FIG. 15).

Figure 8:
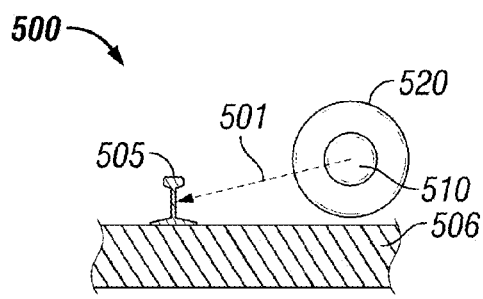
FIG. 8 shows a cross sectional view of an embodiment of a beam generating system having a radiation source and a collimation collar.

FIG. 8 shows a cross sectional view of an embodiment of a beam generating system 500 having a radiation source 510 and a collimation collar 520. The beam generating system 500 may be positioned aside a rail 505 of a railroad track 506 and direct radiation angularly downward toward the rail 505. The beam generating system 500 is configured to direct at least one beam 501 of radiation into a railway track component, such as a rail 505. The at least one beam may be a plurality of beams 501. Radiation is emitted from the radiation source 510 and collimated by the collimation collar 520. The plurality of beams 501 may include at least two beams having a different beam shape. The plurality of beams 501 may include at least one fan beam and at least one rotating pencil beam.

Figure 9:
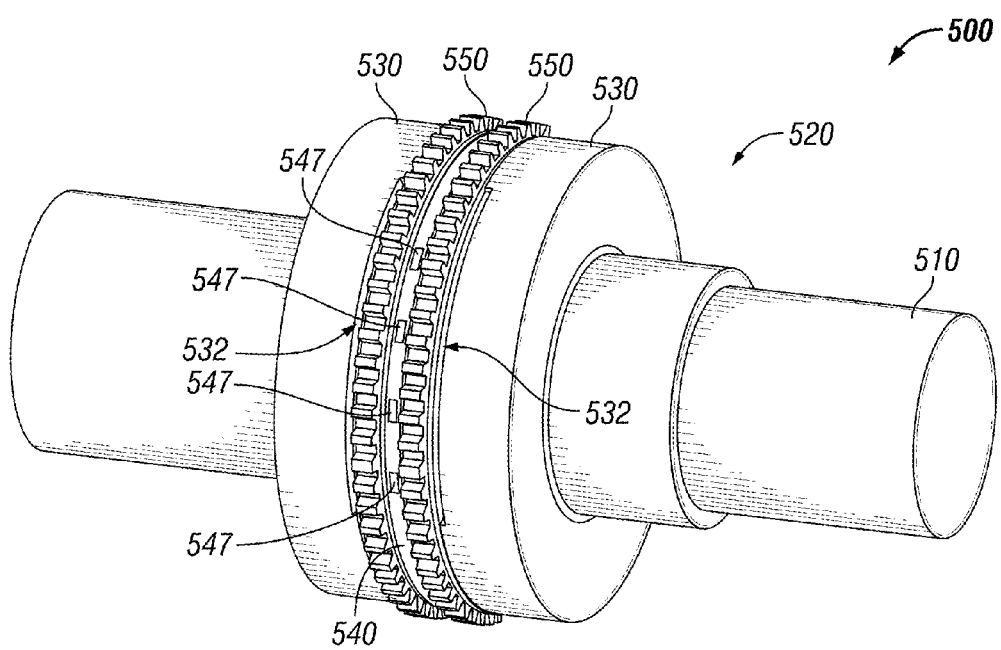
FIG. 9 shows an embodiment of a beam generating system having a radiation source and a collimation collar.

FIG. 9 shows an embodiment of a beam generating system 500 having a radiation source 510 and a collimation collar 520. The radiation source 510 may be an x-ray tube, gamma source, neutron generator, or other energy wave source. The collimation collar 520 includes at least one fan beam collimator 530 and a collimator wheel 540. The collimation collar 520 may include a drive mechanism 550 configured to rotate the collimator wheel 540. In some embodiments, the at least one fan beam collimator 530 is a plurality of fan beam collimators 530. As shown, the collimation collar 520 may be configured to produce a rotating pencil beam and two fan beams. Each fan beam collimator 530 includes a channel 532 shaped to form radiation into a fan beam. The collimator wheel 540 includes beam openings 547 configured to produce a rotating pencil beam as collimator wheel 540 rotates.

Figure 10:
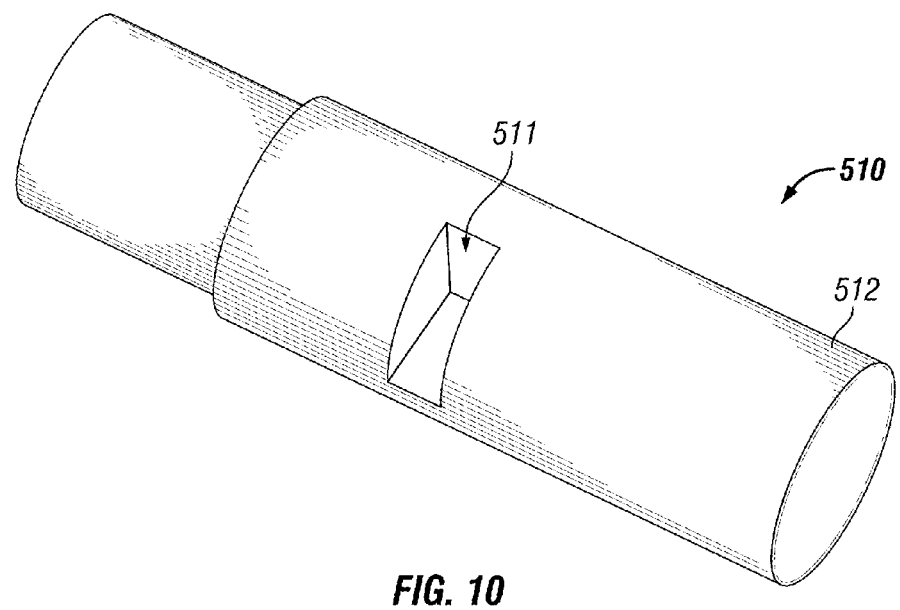
FIG. 10 shows an embodiment of a radiation source.

FIG. 10 shows an embodiment of radiation source 510 with a radiation aperture 511 and a housing 512. A field of radiation is emitted from the radiation source 510 through the radiation aperture 511 of the radiation source 510. The housing 512 of radiation source 510 is configured to absorb radiation from the radiation source 510 and permit radiation to be emitted from radiation aperture 511.

Figure 11:
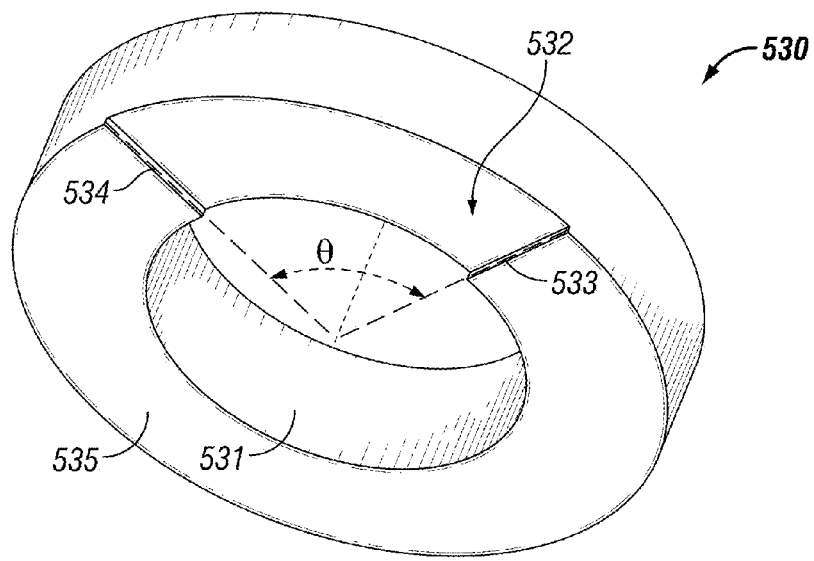
FIG. 11 shows an embodiment of a fan beam collimator.

FIG. 11 shows an embodiment of a fan beam collimator 530. The fan beam collimator 530 includes an inner profile 531 shaped to at least partially surround the housing 512 (shown in FIG. 10) of the radiation source 510 and may comprise a material that blocks or absorbs the type of energy being emitted from the radiation source 510. Radiation from the radiation source 510 is received at the inner portion of the fan beam collimator 530 and directed radially outward. The fan beam collimator 530 includes a channel 532 shaped to collimate radiation into a fan beam. The channel 532 of the fan beam collimator 530 is defined by a first side 533 and a second side 534. The angle $\theta$ between the first side 533 and the second side 534 defines the spread of the fan beam. A depth of the channel 532 of the fan beam collimator 530 defines the thickness of the fan beam. The channel 532 may be an open channel formed in the side 535 of the fan beam collimator 530, as shown. A surface of an adjacent component, such as drive mechanism 550 (shown in FIG. 9), may assist to define the thickness of the fan beam when the channel 532 is an open channel formed in the side 535 of the fan beam collimator 530. The slope of the channel 532 of the fan beam collimator 530 directs the angle of emission of the fan beam. The slope of channel 532 shown in FIG. 11 is zero and radiation may be directed immediately outward. However, the slope of the channel 532 may cause the channel 532 to be formed through the fan beam collimator 530. For example, as discussed above with respect to FIG. 2, the slope of the channel 532 of the fan beam collimator 530 may correspond to the angle $\alpha$ of the forward fan beam 220 or the angle $\beta$ of the rearward fan beam 225 as would be appreciated by one of ordinary skill in the art having the benefit of this disclosure.

Figure 12:
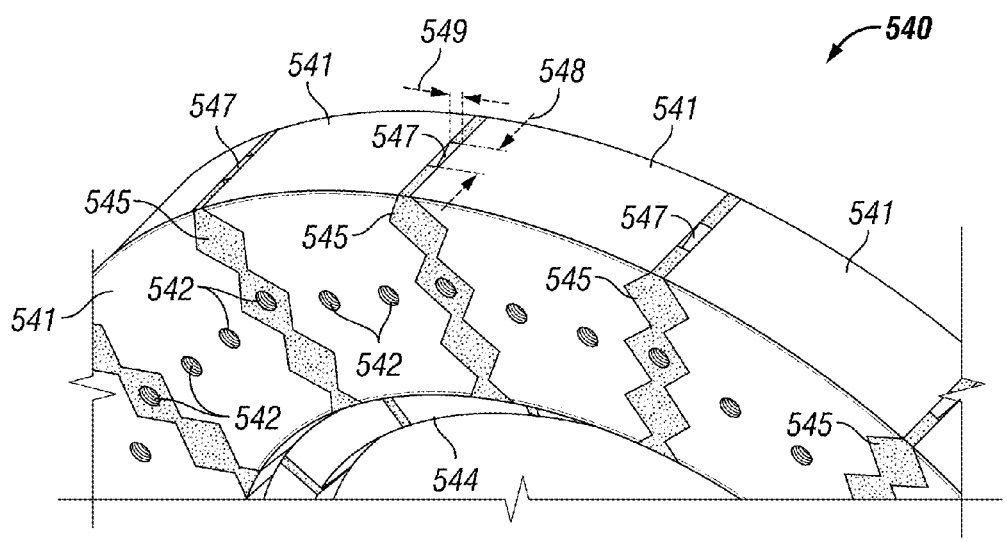
FIG. 12 shows a partial view of an embodiment of a collimator wheel.

FIG. 12 shows a partial view of an embodiment of a collimator wheel 540 having an inner profile 544 shaped to at least partially surround the housing 512 of the radiation source 510 (shown in FIG. 9). The collimator wheel 540 is configured to produce a rotating pencil beam. The collimator wheel 540 includes a plurality of alternating body portions 541 and aperture portions 545. The aperture portions 545 and the body portions 541 may be integral to form an integral collimator wheel 540. In other embodiments, the aperture portions 545 may mate with the body portions 541. The aperture portions 545 and the body portions 541 may comprise a material that blocks the type of radiation being emitted from the radiation source 510 (shown in FIG. 9). The apertures portions 545 each include a beam opening 547 having a width 548 and a height 549. Radiation from the radiation source 510 is received near the inner profile 544 of the collimator wheel 540 and emitted radially outward through the beam openings 547. The spacing between the beam openings 547 of adjacent aperture portions 545 forms an interval angle and determines the resolution and the speed of image creation, including the number of times the target is illuminated per revolution. Larger beam openings 547 may be selected to increase signal by increasing the size of the illumination, and may decrease resolution. Smaller beam openings 547 may be selected to decrease signal but increase resolution. The aperture portions 545 and body portions 541 may include mounts, such as holes 542, configured to connect the collimator wheel 540 to the driving mechanism 550 (shown in FIG. 13). As the driving mechanism 550 is operated, the collimation wheel 540 rotates about an axis substantially perpendicular to the emitted pencil beam 501.

Figure 13:
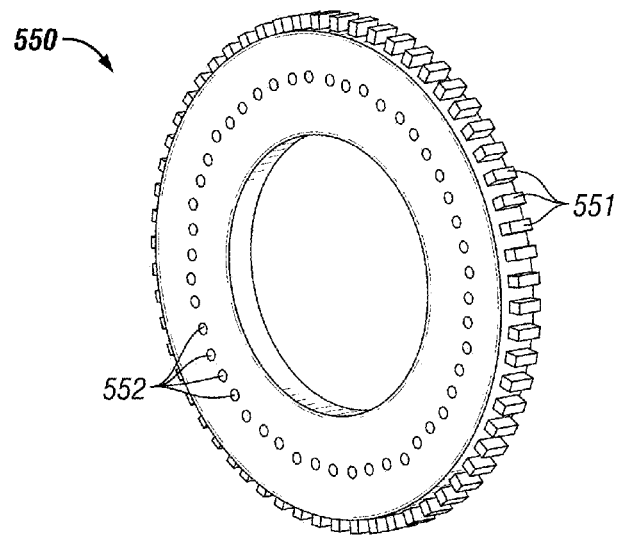
FIG. 13 shows an embodiment of a driving mechanism.

FIG. 13 shows an embodiment of a driving mechanism 550. The driving mechanism 550 is configured to connect to the collimator wheel 540 such that rotation of the driving mechanism 550 causes the collimator wheel 540 to also rotate. The driving mechanism 550 may include teeth 551 shaped mesh with teeth of a gear or belt (not shown). The driving mechanism 550 includes complimentary mounts 552, adapted to connect with the mounts 542 of the collimator wheel 540. In some embodiments, pins 543 (shown in FIG. 14) may rigidly connect the driving mechanism 550 to the collimator wheel 540.

Figure 14:
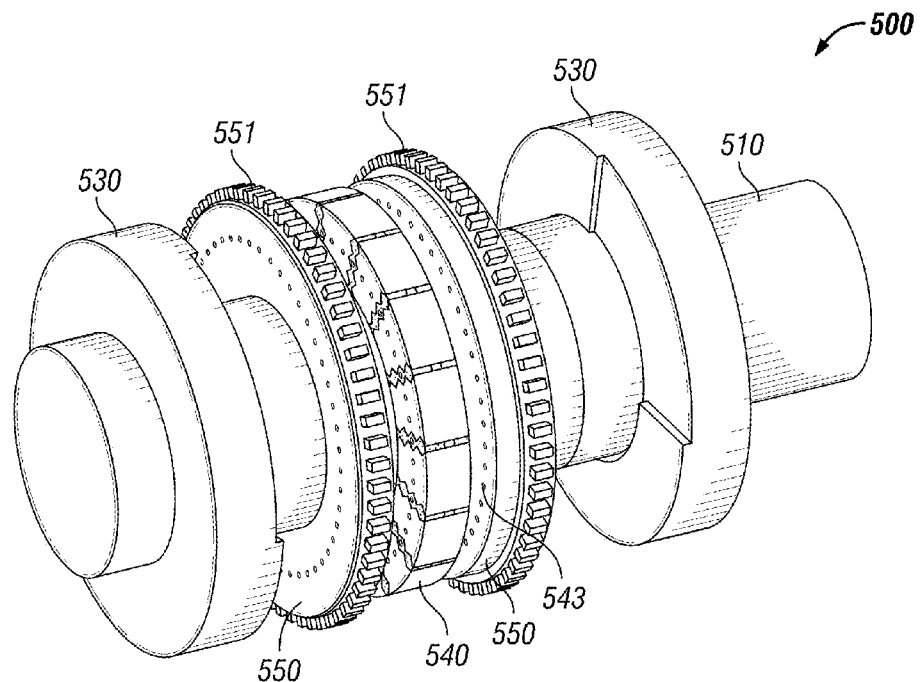
FIG. 14 shows an exploded view of the embodiment of FIG. 9.

FIG. 14 shows an exploded view of beam generating system 500. The collimator wheel 540 is connected on both sides to driving mechanisms 550 via pins 543. A driving gear or belt (not shown) may mesh with the teeth 551 of the driving mechanism 550 to rotate the collimator wheel 540 around the radiation source 510. The radiation source 510 emits a field of radiation from its aperture 511 (best seen in FIG. 10) and toward the collimation collar 520. As the beam openings 547 (shown in FIG. 12) of the collimator wheel 540 intersect the radiation field emitted from the radiation source 510, radiation is collimated through the beam openings 547 and forms a rotating pencil beam. The fan beam collimators 530 are positioned on each side of the collimation wheel 540. The fan beam collimators 530 may be fixed from rotation. Radiation from the radiation source 510 is received into the channel 532 (shown in FIG. 11) of the fan beam collimator 530 and collimated into a fan beam.

In some applications, railroad inspection applications require that certain height clearance thresholds be maintained. For example, the system may need to be compliant with at least one of the Association of American Railroads (AAR) plate F clearance envelope or the AAR plate C clearance envelop. Further, it may be desirable to position the center of a beam of radiation closer to the center of the rail in order to achieve a more desirable illumination perspective for reconstruction. However, the size and positioning of a collimator around a radiation source may hinder the placement of the radiation source and the relative position of the beam of radiation with respect to the rail to be inspected. For example, a rotating collimator may interfere with a crosstie, tie plate, or other object positioned on the track.

Figure 15:
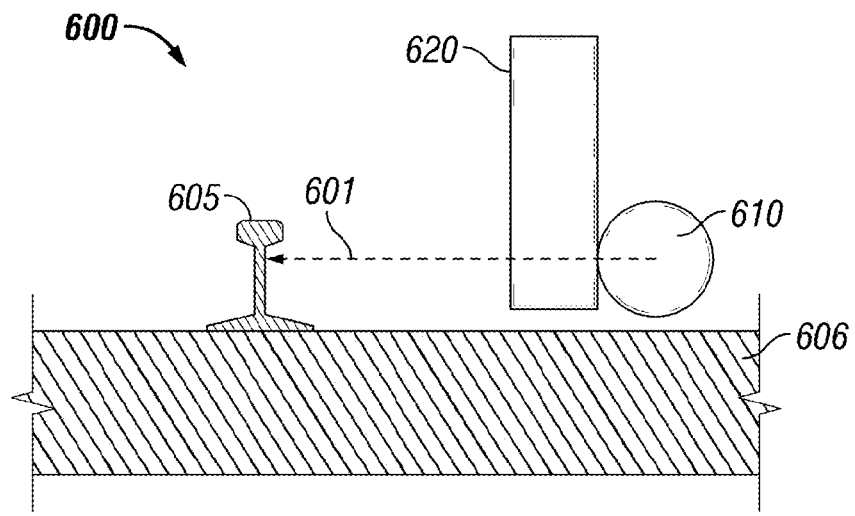
FIG. 15 shows a cross sectional view of an embodiment of a beam generating system including a radiation source and a planar rotating collimator.

FIG. 15 shows a cross sectional view of an embodiment of a beam generating system 600 including a radiation source 610 and a planar rotating collimator 620. The beam generating system 600 is configured to direct at least one beam 601 of radiation into a railway track component, such as a rail 605, of a railroad track 606 at a lower position relative to collimators positioned around a radiation source. The at least one beam 601 may be a plurality of beams 601. The beam generating system 600 may more readily clear track obstacles than other collimator and may achieve a more desirable illumination perspective for reconstruction.

Figure 16:
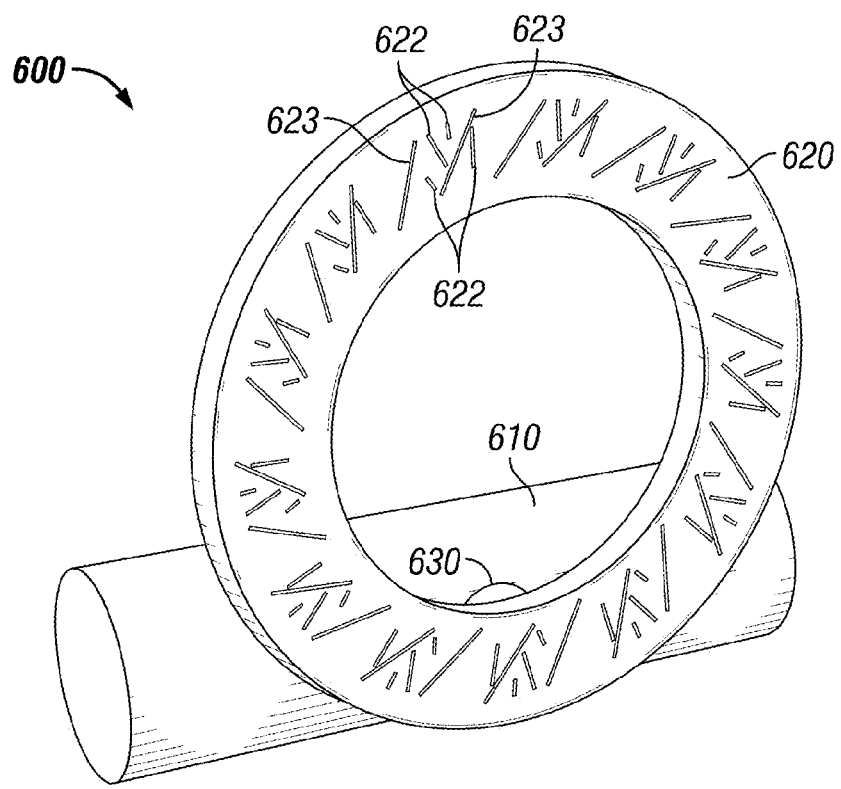
FIG. 16 shows an embodiment of a beam generating system including a radiation source and a planar rotating collimator.

FIG. 16 shows an embodiment of a beam generating system 600 including a radiation source 610 and a planar rotating collimator 620. Radiation is emitted from the radiation source 610 and collimated by the planar rotating collimator 620 into a plurality of beams 601 of radiation. The plurality of beams 601 include at least two beams having a different beam shape. The plurality of beams 601 may include at least one fan beam and at least one rotating pencil beam. As shown, the planar rotating collimator 620 may be configured to produce a rotating pencil beam and two fan beams. The radiation source 610 is positioned adjacent the planar rotating collimator 620 and emits radiation toward the planar rotating collimator 620 in a direction substantially perpendicular to the axis of rotation of the planar rotating collimator 620. The radiation source 610 may be an x-ray tube, gamma source, neutron generator, or other energy wave source.

In some embodiments, the planar rotating collimator 620 may be configured to produce only a rotating pencil beam, as would be appreciated by one of ordinary skill in the art having the benefit of this disclosure. In other embodiments, the planar rotating collimator 620 may be configured to produce only a fan beam or plurality of fan beams, and no rotating pencil beam, as would be appreciated by one of ordinary skill in the art having the benefit of this disclosure.

Figure 17:
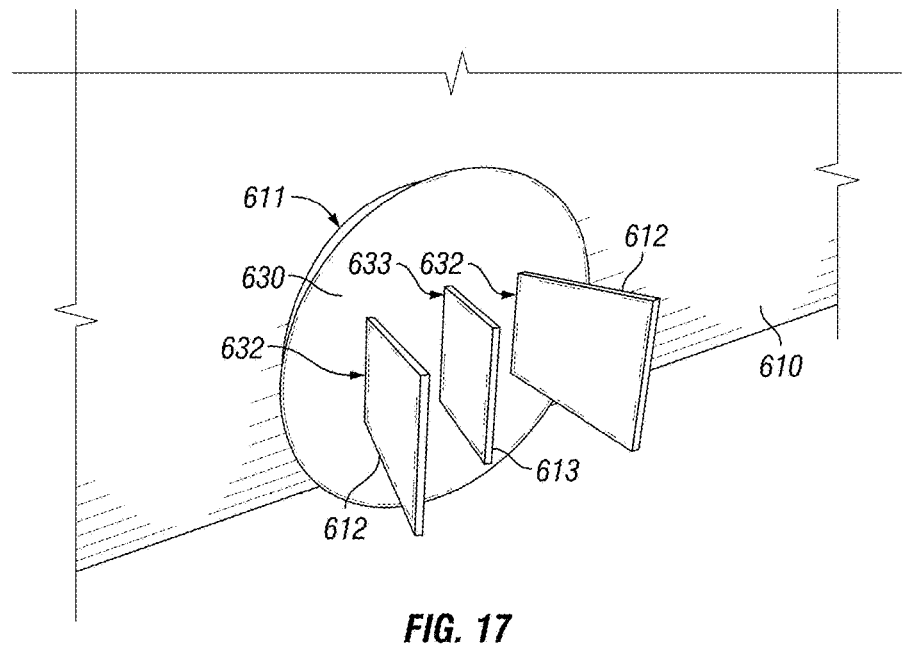
FIG. 17 shows an embodiment of a radiation source and a fixed aperture plate.

FIG. 17 shows an embodiment of the radiation source 610 with a radiation aperture 611 and a fixed aperture plate 630. A radiation field is emitted from the radiation source 610 through the radiation aperture 611 of the radiation source 620. The aperture plate 630 is configured to collimate radiation from the radiation source 610. The aperture plate 630 is received within the radiation aperture 611. As radiation is emitted from the radiation source 610, it is focused or "collimated" so that the radiation only moves in one general path from the radiation source 610 to the target 605 (shown in FIG. 15), thereby reducing undesirable scattered radiation from reaching the target 605.

The aperture plate 630 is fixed to the radiation aperture 611 of the radiation source 610. The aperture plate 630 comprises a material that blocks or absorbs the type of radiation being emitted from the radiation source 610. For example, the aperture plate 630 may comprise lead and the radiation source 610 may be an x-ray source. The aperture plate 630 may comprise polyethylene and the radiation source 610 may be a neutron source. The aperture plate 630 includes a plurality of beam apertures shaped to collimate the field of radiation from the radiation source 610 into a plurality of beams. The beam apertures may be fan beam apertures 632 configured to produce fan beams 612 and pencil beam aperture 633 configured to produce fan beam 613. The planar rotating collimator 620 (shown in FIG. 16) may further collimate and shape the fan beam 613 into a pencil beam and further focus fan beams 612.

Figure 18:
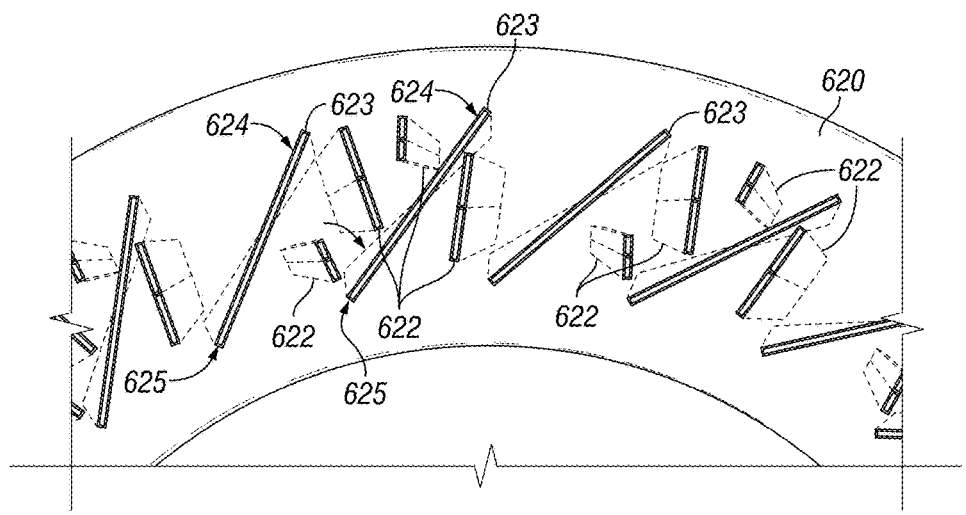
FIG. 18 shows a partial view of an embodiment of a planar rotating collimator.

FIG. 18 shows a partial view of an embodiment of a planar rotating collimator 620. The planar rotating collimator 620 may be made of a material that blocks or absorbs the type of radiation being emitted from the radiation source 610. The planar rotating collimator 620 includes a plurality of beam openings disposed around the planar rotating collimator 620. The planar rotating collimator 620 may be configured to produce a rotating pencil beam and a plurality of fan beams. The beam openings of the planar rotating collimator 620 may include fan beam openings 622 and pencil beam openings 623. The beam openings may be distributed around the planar rotating collimator 620 in a pattern. The pattern, location, shape, angle, curvature, and size of the beam openings may be selected to determine the resolution and speed of image creation. The quantity of the beam openings may determine how many times the target is illuminated per revolution and which portions of the target are illuminated. The shape, angle, curvature, and size of the beam openings correlate to resolution of the image and amount of signal broadcast. Larger beam openings may be selected to increase signal by increasing the size of the illumination, and decreases resolution. Smaller beam openings may be selected to decrease signal but increase resolution.

The pencil beam openings 623 may be angled with respect to the orientation of the fan beam 613 such that only a portion of the pencil beam opening 623 intersect the fan beam 613 (shown in FIG. 17) as the planar rotating collimator 620 rotates. In addition, the pencil beam openings 623 may include varying angles that extend along the length of the pencil beam openings 623 to further direct the portion of the fan beam 613 emitted from the pencil beam openings 623.

In operation, the planar rotating collimator 620 is positioned adjacent to the radiation source 610. The radiation source 610 emits a field of radiation out of its aperture 611 toward planar rotating collimator 620. The aperture plate 630, disposed within the radiation aperture 611 of the radiation source 610, collimates the field of radiation into fan beams 612 and 613 (shown in FIG. 17. A portion of the fan beam 613 aligns with one of the pencil beam openings 623 in the planar rotating collimator 620. As the planar rotating collimator 620 rotates, the position of the pencil beam opening 623 with respect to radiation beam 613 is changed. When first aligned, only a top portion of the fan beam 613 passes through an upper portion 624 of the pencil beam opening 623. As the planar rotating collimator 620 continues to rotate, a lower portion of the fan beam 613 passes through a lower portion of the pencil beam opening 623 and the top portion of beam 613 is no longer aligned with the pencil beam opening 623. The planar rotating collimator 620 continues to rotate until a portion of the radiation beam 613 passes through the lowest portion 625 of the pencil beam opening 623. Further rotation of the planar rotating collimator 620 aligns the top portion of beam 613 with an upper portion 624 of an adjacent pencil beam opening 623. Accordingly, the portion of beam 613 that passes through the pencil beam opening 623 sweeps the target, as described above, to produce a rotating pencil beam profile 250 (shown in FIG. 3).

The fan beams 612 from fan beam apertures 632 (shown in FIG. 17) are directed toward planar rotating collimator 620. As the planar rotating collimator 620 rotates, the fan beam openings 622 may align with at least a portion of the fan beams 612. The fan beam openings 622 further collimate the fan beams 612 into shuttered fan beams. The number and orientation of the fan beams apertures 632 of the aperture plate 630 and the number and orientation of the fan beam openings 622 of the planar rotating collimator 620 may be selected to achieve a desired beam profile.

Figure 19:
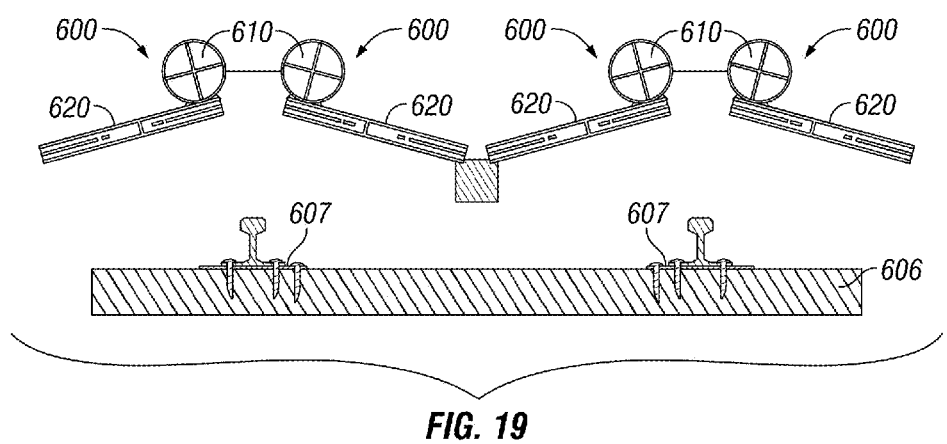
FIG. 19 shows a plurality of beam generating systems oriented to irradiate multiple portions of railway components on a railroad track.

FIG. 19 shows a plurality of the beam generating systems 600 oriented to irradiate multiple portions of railway components, such as tie plates 607, on a railroad track 606. The plurality of beam generating systems 600 may be oriented to illuminate multiple sides of the railway component. Further, unlike the orientation of the generating system 600 shown in FIG. 15, the orientation of the beam generating systems 600 in FIG. 19 might only use backscatter radiography, if a transmission detector is not positioned on the opposing side of the railroad component being inspected.

Figure 20:
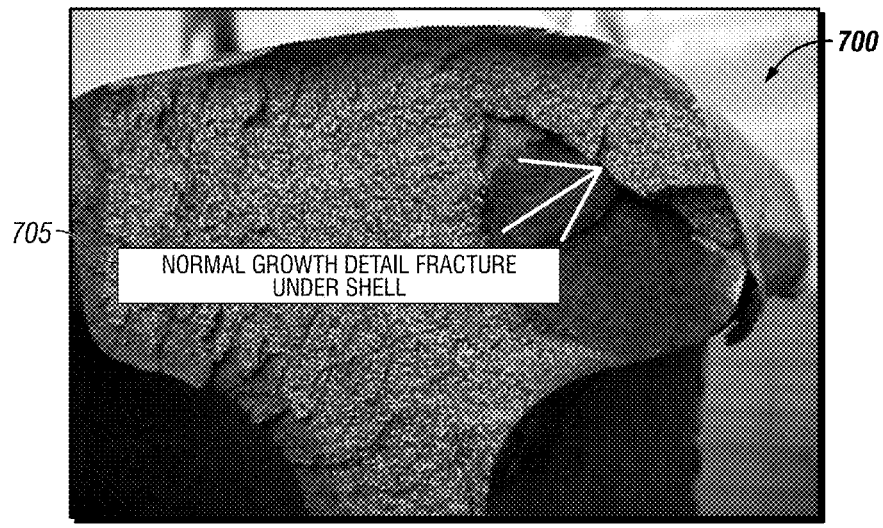
FIG. 20 shows an example of an under shell facture in a rail.
Figure 21:
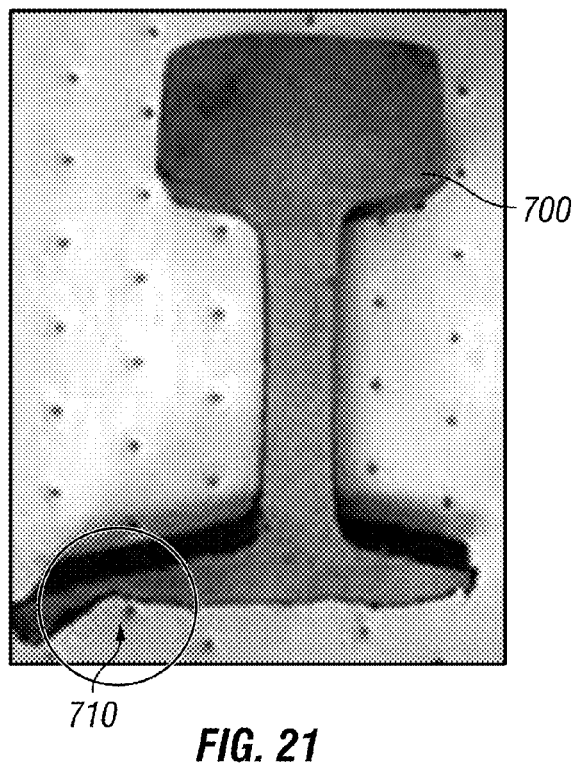
FIG. 21 shows an example of Rail Base Corrosion.
Figure 22:
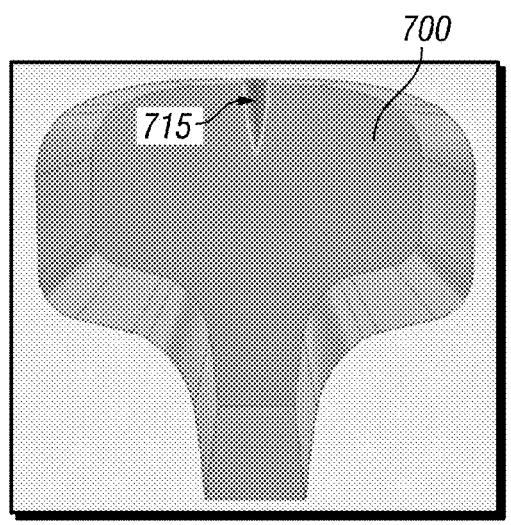
FIG. 22 shows an example of a crack in a head portion of a rail.
Figure 23:
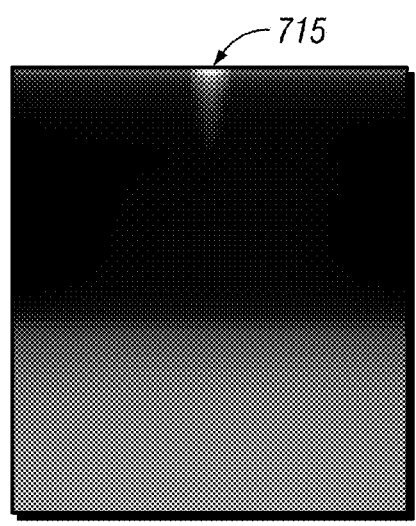
FIG. 23 shows a generated pixilated gray-scale image of FIG. 22.
Figure 24:
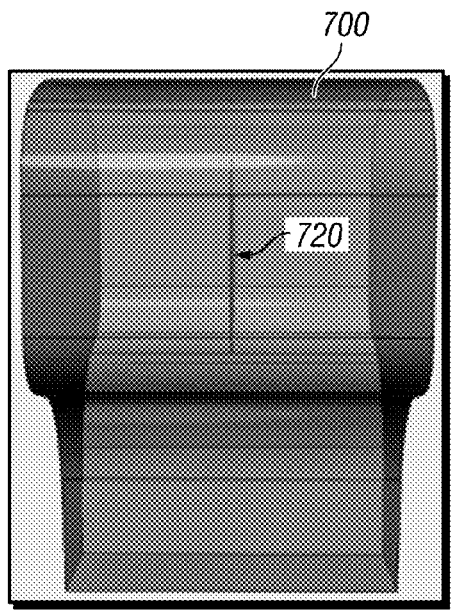
FIG. 24 shows an example of a void in a rail.
Figure 25:
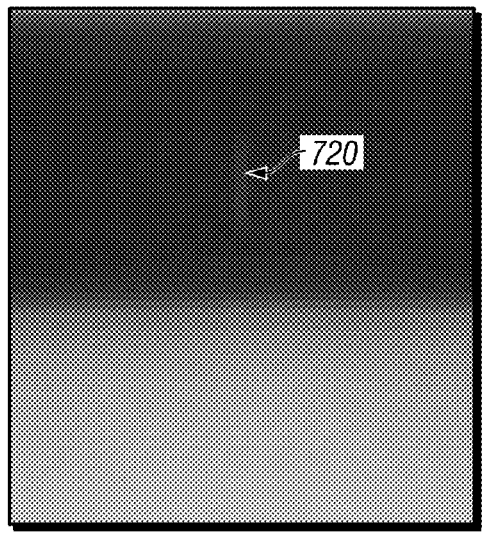
FIG. 25 shows a generated pixilated gray-scale image of FIG. 24.

The internal inspection system 100 (shown in FIG. 1) may be used to detect and/or identify various flaws or anomalies within railway components. For example, the system 100 may be used to detect an under shell fracture 705 in a rail 700 as shown in FIG. 20 or Rail Base Corrosion (RBC) 710 on a rail 700 as shown in FIG. 21. FIG. 22 shows an example of a crack 715 in a head portion of a rail 700 used in a simulation. FIG. 23 shows a pixilated gray-scale image of the rail 700 with the crack 715 in the rail 700, as may be generated by the internal inspection system 100. FIG. 24 shows an example of a void 720 in the rail 700 used in a simulation. FIG. 25 shows a pixilated gray-scale image of the rail 700 with the void 720 in the rail 700, as may be generated by the internal inspection system 100.

Figure 26:
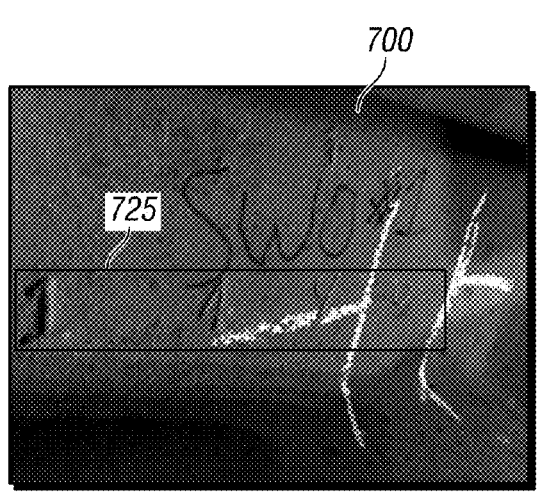
FIG. 26 shows hot numbers stamped on the web of a rail.
Figure 27:
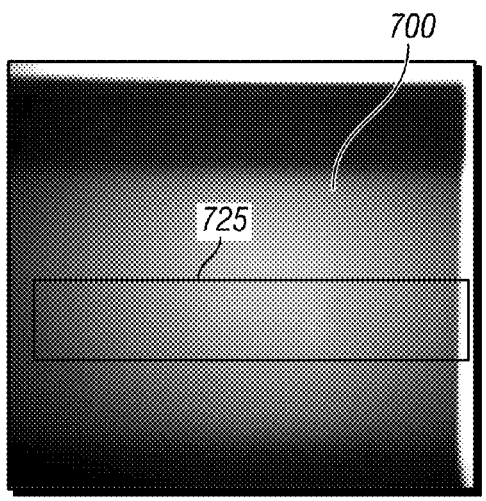
FIG. 27 shows a generated pixilated gray-scale image of FIG. 26.
Figure 28:
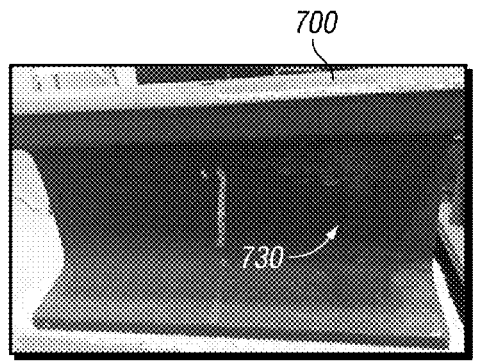
FIG. 28 shows a protrusion positioned on the web of a rail.
Figure 29:
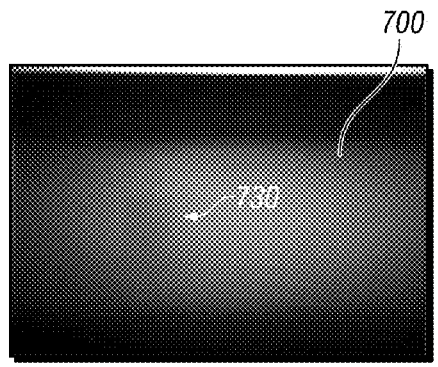
FIG. 29 shows a generated pixilated gray-scale image of FIG. 28.
Figure 30:
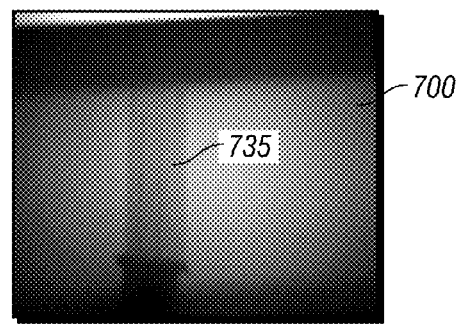
FIG. 30 shows a generated pixilated gray-scale image of a turbine blade positioned behind a rail.

FIG. 26 shows hot numbers 725 stamped on the web of the rail 700. FIG. 27 shows a pixilated gray-scale image of the rail 700 with the stamped numbers 725 on the web of the rail 700, as generated by the internal inspection system 100 using neutron radiography. It is noted that the pixilated gray-scale image is a mirror image of the rail in FIG. 26. FIG. 28 shows a protrusion 730 positioned on the web of the rail 700. FIG. 29 shows a pixilated gray-scale image of the rail 700 with the protrusion 730 on the web of the rail 700, as generated by the internal inspection system 100 using neutron radiography. FIG. 30 shows a pixilated gray-scale image of a turbine blade 735 positioned behind the rail 700, as generated by the internal inspection system 100 using neutron radiography.

Figure 31:
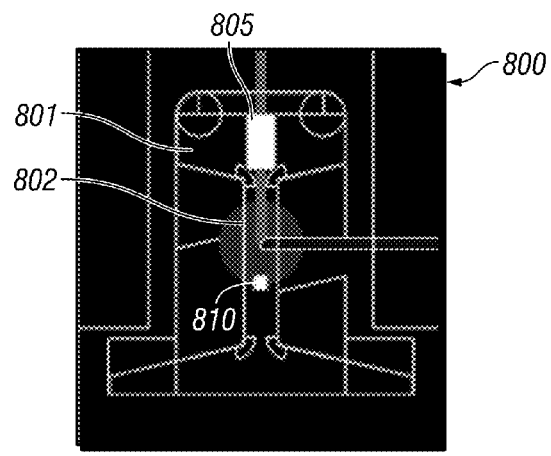
FIG. 31 shows a cross sectional view of a defective rail having a head void and a web void.
Figure 32:
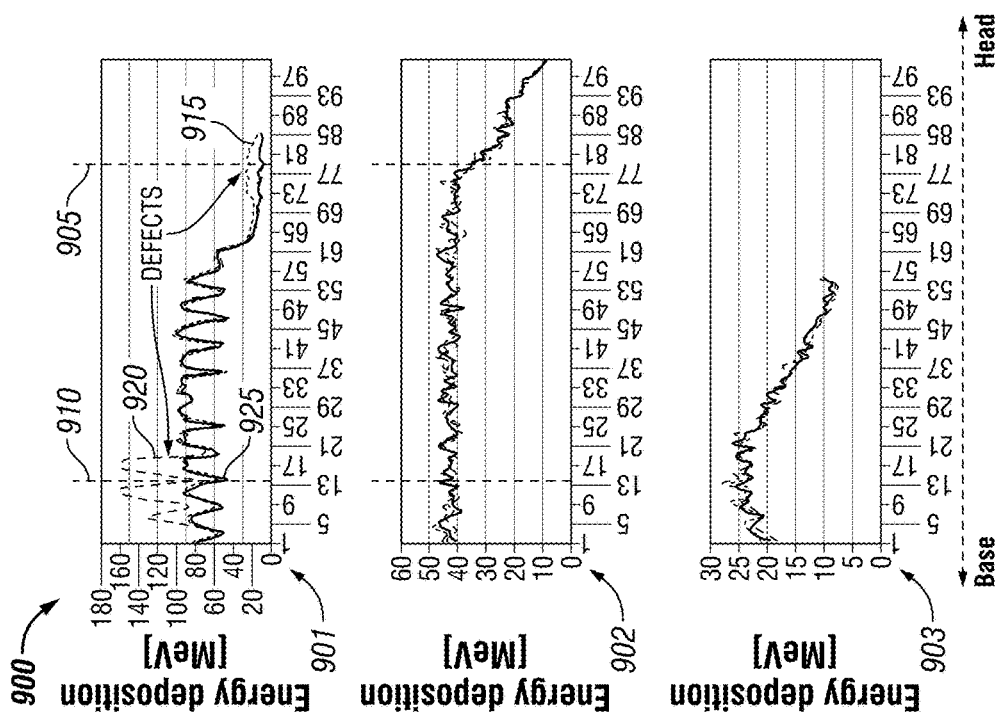
FIG. 32 shows a signal chart that was generated using a fan beam geometry.

FIG. 31 shows a cross sectional view of a defective the rail 800 used in simulations. The defective the rail 800 includes a head 801 having the head void 805 measuring 2 cm×1 cm and a web 802 having a web void 810 measuring 1 cm×1 cm. FIG. 32 shows a signal chart 900 that was generated using a fan beam geometry. The chart 900 consists of transmission detector signals 901, top scatter detector signals 902, and backscatter detector signals 903. The left side of the chart 900 shows readings from the base of the rail that extend towards the head of the rail on the right side of the chart 900. Line 905 on chart 900 corresponds to the location of the head void 805 of the rail 800 (shown in FIG. 31). Line 910 on chart 900 corresponds to the location of web void 810 of the rail 800 (shown in FIG. 31). As shown, the transmission detector signals 901 yielded contrast results, while the top scatter and backscatter signals 902, 903 provided less information. The transmission detector signals 901 include signals 915 corresponding to the head void 805 of the rail 800 (shown in FIG. 31), signals 920 corresponding to web void 810 of the rail 800 (shown in FIG. 31), and signals 925 corresponding to a rail having no defect. The energy levels of signals 915 at line 905 and signals 920 at line 910 indicate the presence of voids 805 and 810 in the rail 800 (shown in FIG. 31).

Figure 33:
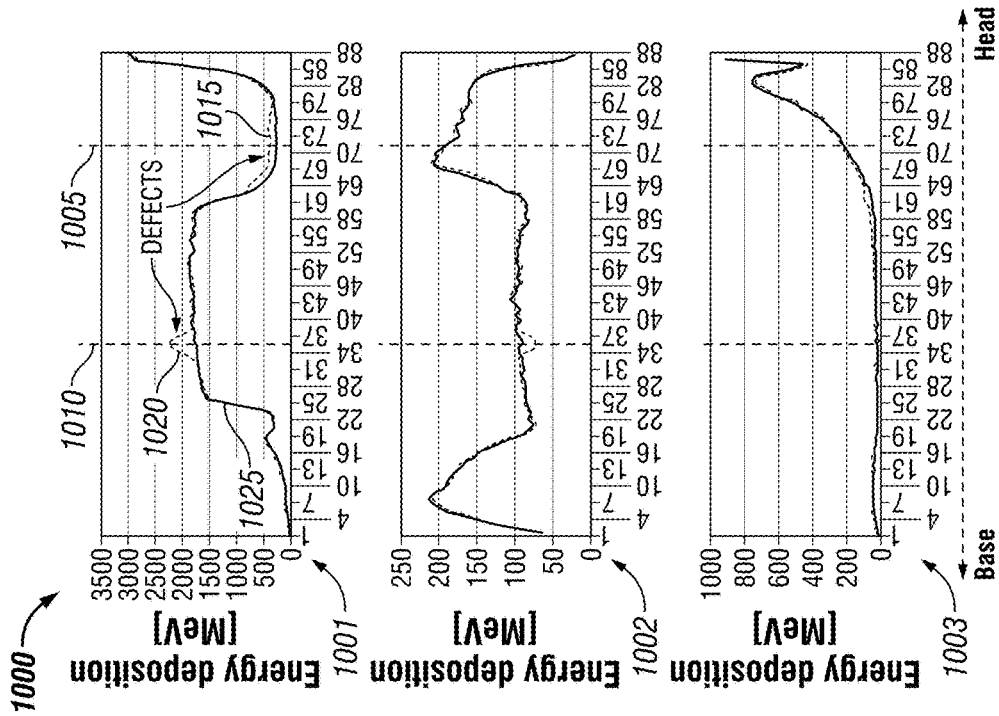
FIG. 33 shows a signal chart that was generated using a pencil beam geometry.

FIG. 33 shows a signal chart 1000 that was generated using a pencil beam geometry. The chart 1000 consists of transmission detector signals 1001, top scatter detector signals 1002, and backscatter detector signals 1003. The left side of the chart 1000 shows readings from the base of the rail that extend towards the head of the rail on the right side of the chart 1000. Line 1005 on chart 1000 corresponds to the location of the head void 805 of the rail 800 (shown in FIG. 31). Line 1010 on chart 1000 corresponds to the location of web void 810 of the rail 800 (shown in FIG. 31). As shown, the transmission detector signals 1001 yielded better resolution than the transmission detector signals 901 (shown in FIG. 32) but provided a lower contrast compared to signals 901 of the fan beam geometry. Furthermore, the top scatter detector signals 1002 and backscatter detector signals 1003 may provide more useful information, such as three-dimensional position, than the top scatter and backscatter signals 902, 903 of the fan beam geometry. The transmission detector signals 1001 include signals 1015 corresponding to the head void 805 of the rail 800 (shown in FIG. 31), signals 1020 corresponding to web void 810 of the rail 800 (shown in FIG. 31), and signals 1025 corresponding to a rail having no defect. The energy levels of signals 1015 at line 1005 and signals 1020 at line 1010 indicate the presence of voids 805 and 810 in the rail 800 (shown in FIG. 31).

Figure 34:
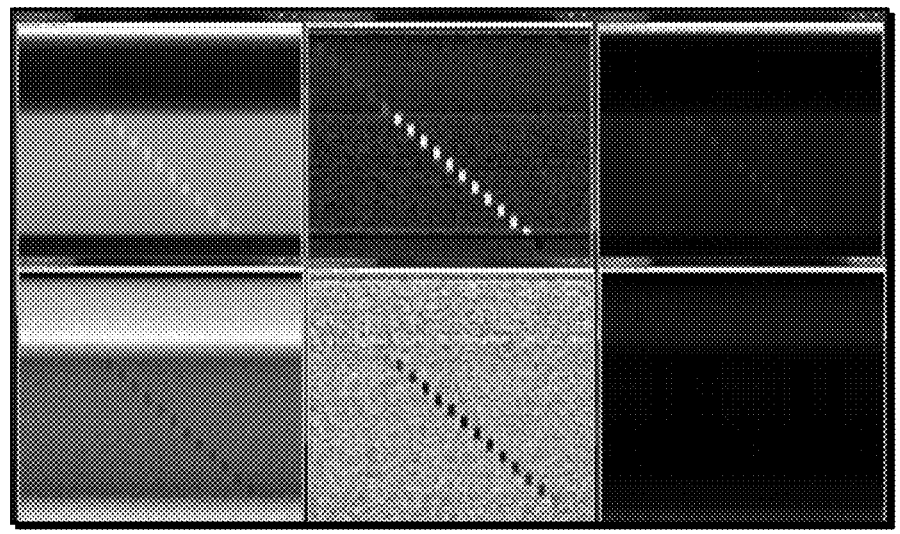
FIGS. 34-36 show simulated images of inspection of defects in a rail.
Figure 35:
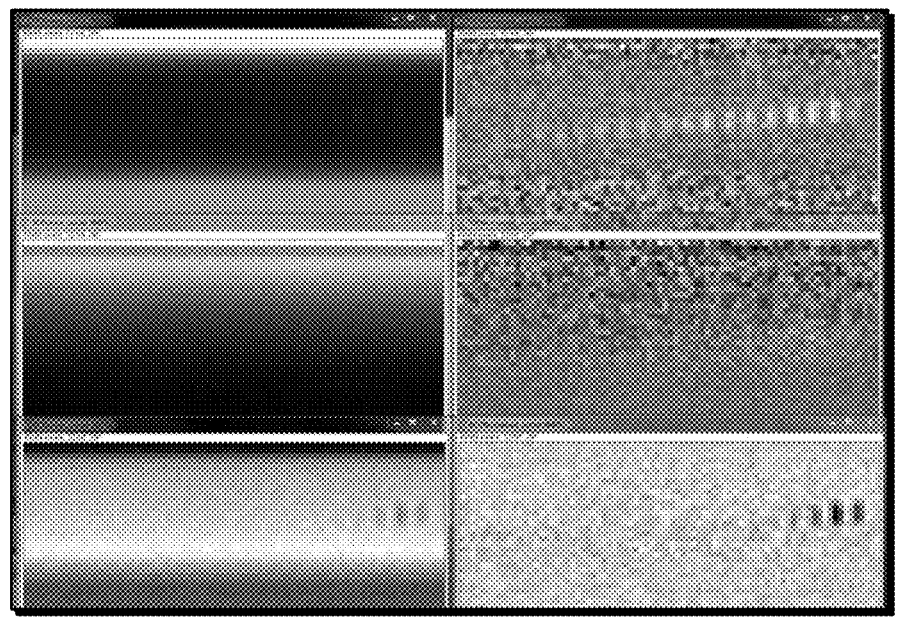
Figure 36:
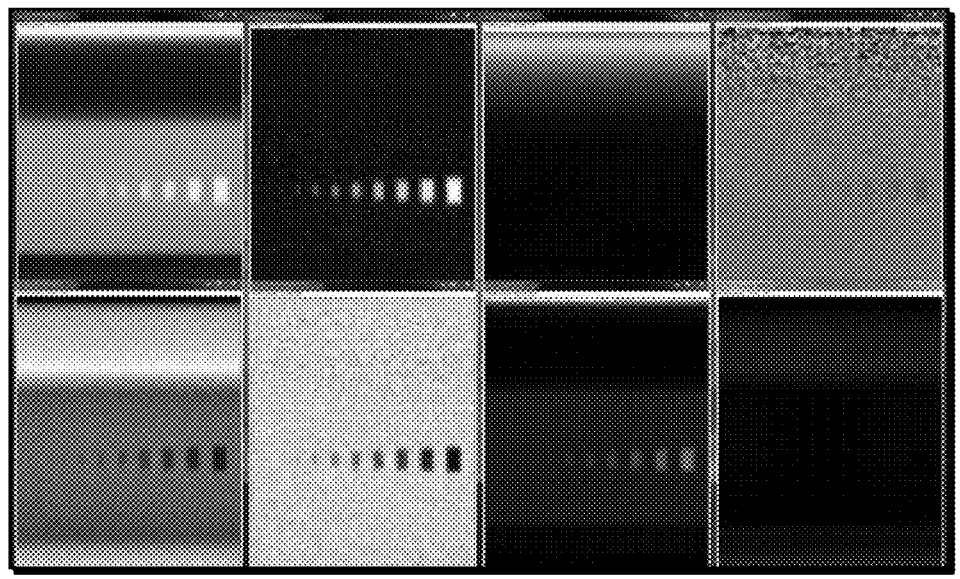
Figure 37:
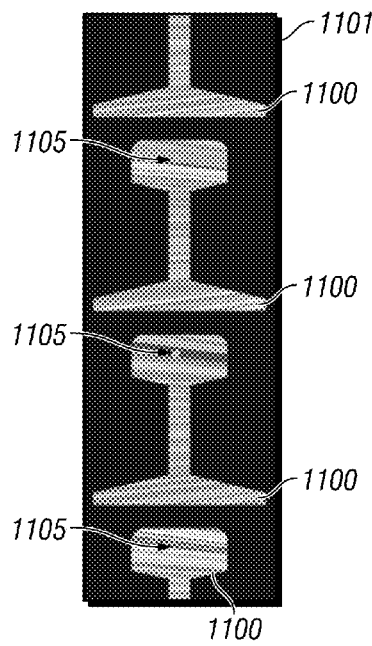
FIG. 37 shows simulated 3D CT images of a defect in a head of a rail.

FIG. 34 shows simulated images of inspection of defects across an entire rail using a pencil beam. FIG. 35 shows simulated images of inspection of defects across a rail head using a pencil beam. FIG. 36 shows simulated images of inspection of defects across a rail web using a pencil beam. FIG. 37 shows simulated 3D CT images 1101 of a defect 1105 in the head of a rail 1100 as may be generated by internal inspection system 100 (shown in FIG. 1). Initially, 2D images were generated by using a number of different image processing methods. A 2D image model was generated using transmission detector data alone and was able to identify defects as small as 1 mm in the web and 3 mm in the head. The 3D CT images 1101 were generated using combined data strings from both fan beam and pencil beam and signals from nine detectors. Using the combination of data strings from both fan beam and pencil beam, a 3D image reconstruction may be generated in real time.

Figure 38:
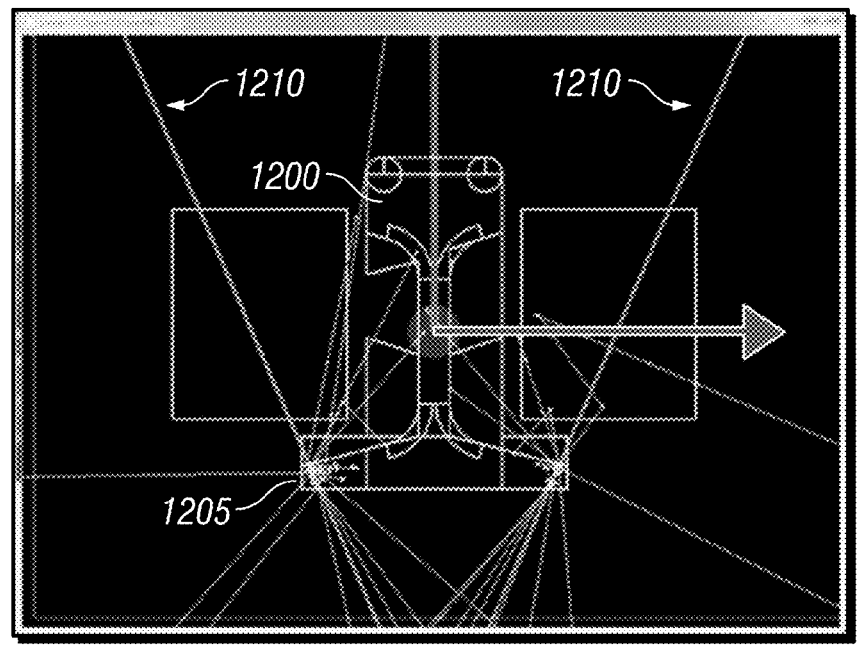
FIG. 38 shows a cross-sectional view of simulated models of a rail base and tie plate and backscattered radiation.
Figure 39:
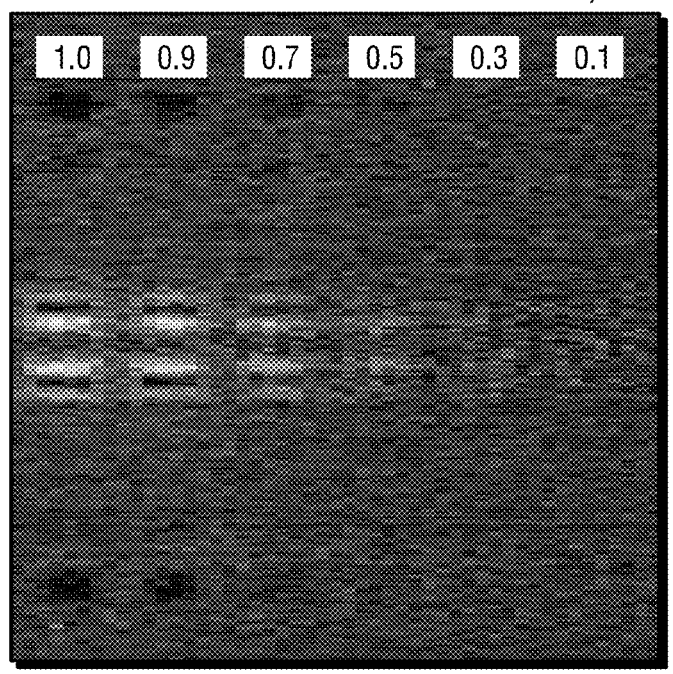
FIGS. 39-41 shows backscatter images from a model rail containing defects in lower parts of the rail web.
Figure 40:
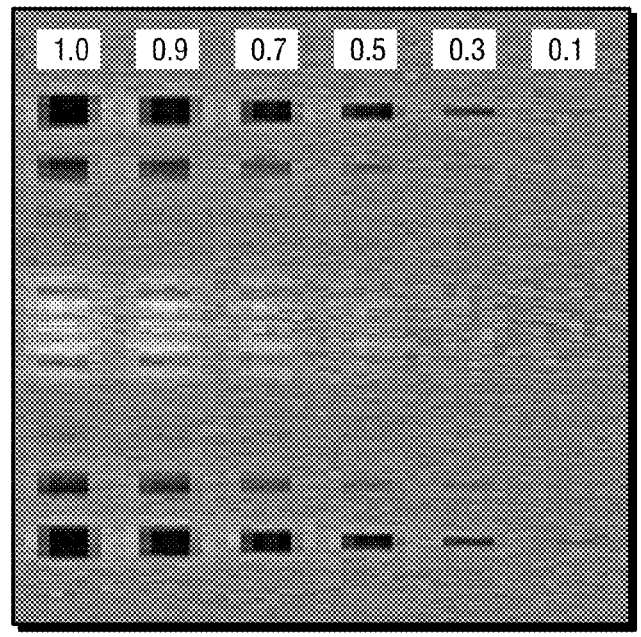
Figure 41:
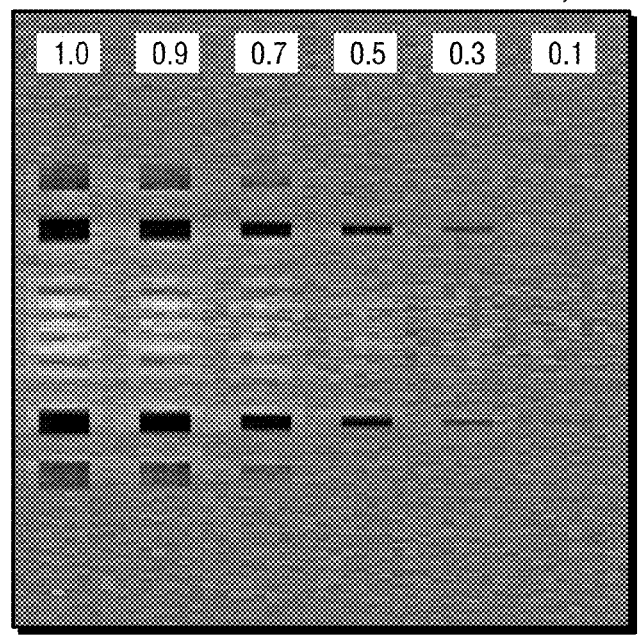
Figure 42:
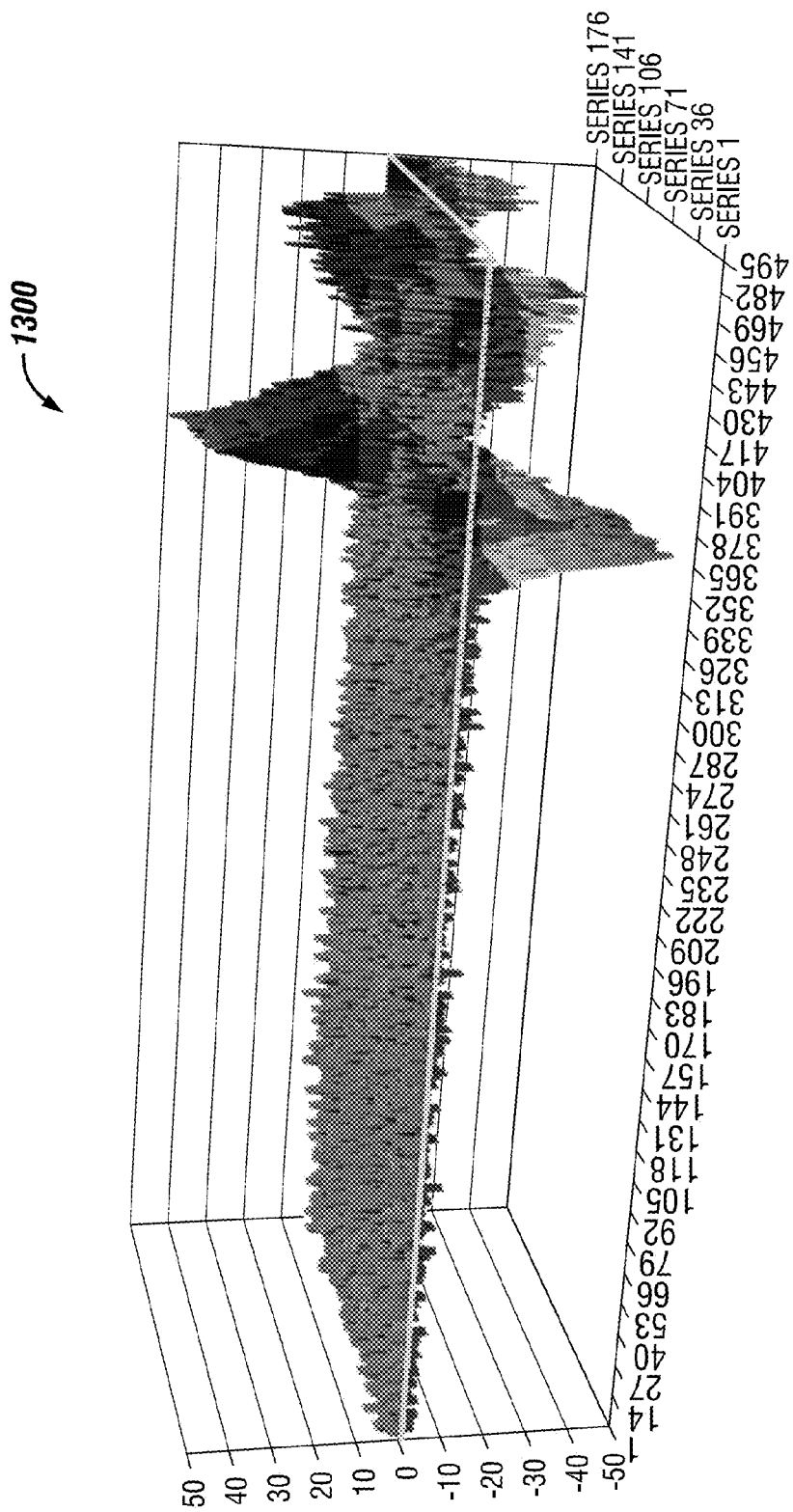
FIG. 42 shows a generated 3D profile of three off-centered defects at a lower part of a web.

FIG. 38 shows a cross-sectional view of simulated models of a rail head 1200, rail base 1205, and backscattered radiation. Radiation 1210 is directed into the rail base 1205 at an angle and scattered by interaction with the rail base 1205. The simulation shows the difference of the backscatter images between different surroundings, such as wood crosstie, concrete crosstie, ballast etc. A series of solid rail profile may be generated and used to normalize image processing and 3D image reconstruction. FIGS. 39-41 shows backscatter images from a model rail containing defects in lower parts of a rail web using 0.2 cm collimation spacing and backscatter radiography. FIG. 39 shows a scan of defects ranging in size from 0.1 cm to 1.0 cm positioned on the bottom of a rail base. FIG. 40 shows a scan of defects ranging in size from 0.1 cm to 1.0 cm positioned 1.0 cm above the bottom of the rail base. FIG. 41 shows a scan of defects ranging in size from 0.1 cm to 1.0 cm positioned 2.0 cm above the bottom of the rail base. As shown in FIGS. 39-41, larger defects, such as 3 mm or more, may be more easily shown from the backscatter images. In addition, defects closer to the surface may more easily be shown from the backscatter images. FIG. 42 shows a generated 3D profile 1300 of three off-centered defects at the lower part of a web of a rail. After a number of image processing steps, the 3D profile 1300 shows that these defects are off center, the size of the defects, and the position of the defects. With additional correlations using data from fan beam and rotating pencil beam geometries, 3D image (CT) reconstruction may be used to identify both the size and position of defects within a railway component.

Although this disclosure has been described in terms of certain preferred embodiments, other embodiments that are apparent to those of ordinary skill in the art, including embodiments that do not provide all of the features and advantages set forth herein, are also within the scope of this disclosure. Accordingly, the scope of the present disclosure is defined only by reference to the appended claims and equivalents thereof.

What is claimed is:

1. An internal imaging system, the system comprising:
   a radiation source configured to irradiate a railway track component with a plurality of collimated beams of radiation, wherein the radiation source is not an x-ray source;
   a plurality of detectors positioned to receive attenuated portions of the plurality of collimated beams, the plurality of detectors including at least one transmission detector; and
   a vehicle configured to travel along a railway track, the radiation source and the plurality of detectors are connected or mounted to the vehicle.

2. The system of claim 1, wherein the plurality of collimated beams are positioned to irradiate the railway track component at the same time, and wherein two of the plurality of collimated beams of radiation have different beam shapes.

3. The system of claim 2, further comprising a planar rotating collimator positioned adjacent to the radiation source and configured to form the plurality of collimated beams.

4. The system of claim 3, wherein the radiation source includes a fixed aperture having an opening shaped to form a first fan beam, and the planar rotating collimator includes a pencil beam opening, wherein the first fan beam intersects a portion of the pencil beam opening.

5. The system of claim 1, wherein the radiation source is a neutron source and the plurality of detectors is a plurality of neutron converters.

6. The system of claim 5, wherein the plurality of neutron converters includes a neutron scintillator.

7. The system of claim 1, wherein the plurality of collimated beams includes at least one fan beam and a rotating pencil beam.

8. The system of claim 7, wherein the at least one fan beam is a plurality of fan beams.

9. The system of claim 8, wherein the rotating pencil beam is positioned between two of the plurality of fan beams.

10. The system of claim 7, further comprising a collimating collar having:
    at least one fan beam collimator disposed around the radiation source, each of the at least one fan beam collimator having a channel shaped to form radiation passing though the channel into one of the at least one fan beam; and
    a collimator wheel rotatably disposed around the radiation source, the collimator wheel including a plurality of beam openings, wherein radiation passing through the plurality of beam openings as the collimator wheel rotates around the radiation source forms the rotating pencil beam.

11. The system of claim 1, wherein the plurality of detectors includes at least one scatter detector.

12. The system of claim 11, wherein the at least one scatter detector includes backscatter detectors positioned adjacent the radiation source.

13. The system of claim 1, wherein the railway track component is a rail, the transmission detector being positioned to receive a portion of the plurality of collimated beams attenuated by a portion of the rail.

14. A method of using an internal imaging system to inspect a target, the method comprising:

emitting radiation from a radiation source;

collimating the emitted radiation to include a first fan beam and at least one second fan beam;

rotating a planar rotating collimator, the planar rotating collimator including a pencil beam opening shaped to intersect a portion of the first fan beam and form a rotating pencil beam and at least one fan beam opening shaped to receive the at least one second fan beam and form a second beam shape when the at least one fan beam opening is aligned with the at least one second fan beam;

irradiating a target with a plurality of collimated beams of radiation, the plurality of collimated beams being positioned to irradiate the target at the same time, wherein the plurality of collimated beams include a first beam having a first beam shape, the rotating pencil beam being the first beam shape, and a second beam having the second beam shape, the first beam shape being different from the second beam shape;

detecting a strength of a portion of the first beam that has been attenuated by interaction with the target with at least one first detector;

detecting a strength of a portion of the second beam that has been attenuated by interaction with the target with at least one second detector; and generating data relating to an internal characteristic of the target using the detected strengths.

15. The method of claim 14, further comprising irradiating each of a plurality of targets with the plurality of collimated beams of radiation.

16. The method of claim 14, wherein the the second beam is a fan beam.

17. The method of claim 14, further comprising determining an angular position of the rotating pencil beam.

18. The method of claim 14, wherein the radiation is from a neutron source and the at least one first detector and the at least one second detector are neutron converters.

19. The method of claim 14, wherein the at least one first detector includes at least one of a transmission detector or a scatter detector.

20. The method of claim 14, further comprising producing a three-dimensional representation of the target from the data.

21. The method of claim 20, wherein producing the three-dimensional representation of the target from the data comprises producing a three-dimensional representation of the target from the data at an off-site location.

22. An internal imaging system, the system comprising:

a radiation source configured to irradiate a target with at least one collimated beam of radiation including at least one fan beam, the radiation source including a fixed aperture having one or more openings shaped to form at least one second fan beam;

a planar rotating collimator positioned adjacent to the radiation source and configured to form the at least one collimated beam, the planar rotating collimator including at least one fan beam opening shaped to receive the at least one second fan beam and form the at least one fan beam when the at least one fan beam opening is aligned with the at least one second fan beam; and at least one detector positioned to receive attenuated portions of the at least one collimated beam.

23. The system of claim 22, wherein the at least one collimated beam is a plurality of collimated beams including the at least one fan beam and a rotating pencil beam.

24. The system of claim 23, wherein the fixed aperture has an opening shaped to form a first fan beam, and the planar rotating collimator includes a pencil beam opening, wherein the first fan beam intersects a portion of the pencil beam opening to form the rotating pencil beam.

25. The system of claim 22, further comprising a vehicle, the radiation source and the at least one detector are connected or mounted to the vehicle.

26. The system of claim 25, wherein the vehicle is configured to travel along a railway track.

27. The system of claim 22, wherein the radiation source is a neutron source and the at least one detector is at least one neutron converter.

28. The system of claim 27, wherein the at least one neutron converter includes a neutron scintillator.

29. The system of claim 22, wherein the at least one collimated beam is a plurality of collimated beams including the at least one fan beam and a rotating pencil beam, the at least one second fan beam is a plurality of second fan beams, and the at least one fan beam is a plurality of fan beams.

30. The system of claim 29, wherein the rotating pencil beam is positioned between two of the plurality of fan beams.

* * * * *